(12) United States Patent
Swayze et al.

(10) Patent No.: US 6,316,623 B1
(45) Date of Patent: Nov. 13, 2001

(54) ETHYLENEDIAMINE COMPOUND LIBRARIES

(75) Inventors: Eric Edward Swayze, Carlsbad; Elizabeth Anne Campbell Jefferson, San Diego, both of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/138,186

(22) Filed: Aug. 21, 1998

(51) Int. Cl.$^7$ .................................................. C07D 403/00
(52) U.S. Cl. ......................... 544/372; 544/242; 544/372; 544/384; 544/406; 546/245; 546/246; 548/531; 435/7.1; 435/DIG. 2; 435/DIG. 9; 435/DIG. 14; 435/DIG. 22; 435/DIG. 34; 435/DIG. 40; 435/DIG. 42; 435/DIG. 44; 435/DIG. 45; 435/DIG. 46; 435/DIG. 48; 436/518; 436/536
(58) Field of Search ..................................... 544/372, 242, 544/384, 406; 548/531; 546/245, 246; 435/7.1, DIG. 2, 9, 14, 22, 34, 40, 42, 44, 45, 46, 48; 436/518, 536

(56) References Cited

U.S. PATENT DOCUMENTS

| | | | |
|---|---|---|---|
| 4,596,819 | * 6/1986 | Nicolaides et al. | 514/423 |
| 5,175,158 | * 12/1992 | Eberlein et al. | 514/220 |
| 5,726,188 | * 3/1998 | Takano et al. | 514/326 |

FOREIGN PATENT DOCUMENTS

| | | | |
|---|---|---|---|
| 199 55 794 A1 | * 11/1999 | (DE) . | |
| 2 343 893 | * 5/2000 | (GB) . | |
| 1550357 | * 8/1979 | (GB) | A01N/9/28 |
| 8-259562 | * 10/1996 | (JP) | A01N/43/50 |
| 2000069432 | * 11/2000 | (WO) . | |
| 95/07905 | * 3/1995 | (WO) | C07D/401/04 |

OTHER PUBLICATIONS

CAS Abstract No. 1998: 530590. Swazye et al., "Design and Automated Parallel Synthesis of Ethylenediamine Derivatized Heterocyclic Combinatorial Libraries Targeted to Structured RNA," Book of Abstracts, 216th ACS National Meeting, Boston, Aug. 23–27, (19, 1998.*

Nicolaides et al., Modified Di– and Tripeptides of the C–terminal Portion of Oxytocin and Vasopressin as Possible Cognition Activation Agents, J. Med. Chem., 29(6), pp. 959–971, 1986.*

Database Chemical Abstracts on STN, AN 1998:80371, Sigmna–Aldrich Library of Rare Chemicals, Dec. 1995.*

Achari, A. et al., "Facing up to Membranes: Structur/Function Relationships in Phospholipases", *Cold Spring Harbor Symp. Quant. Biol.*, 1987, vol. 52, Cold Spring Harbor Laboratory, 441–452.

Atherton, E. et al., "The Fluorenylmethoxycarbonyl Amino Protecting Group", *The Peptides*, Udenfriend, S. et al. (eds.), 1987, 9, 1–39.

Bomalaski, J.S. et al., "Human Extracellular Recombinant Phospholipase $A_2$ Induces an Inflamatory response in Rabbit Joints", *J. Immunol.*, 1991, 146, 3904–3910.

Brennen, T. et al., "Two–Dimensional Parallel Array Technology as a New Approach to Automated Combinatorial Solid Phase Organic Synthesis", *Biotech. & Bioengin.*, 1998, 61, 33–45.

Burack, W.R. et al., "Role of Lateral Phase Separation in the Modulation of Phospholipase $A_2$ Activity", *Biochemistry*, 1993, 32, 583–589.

Campbell, M.M. et al., "Inhibition of Phospholipase $A_2$; a Molecular Recognition Study", *J. Chem. Soc. Chem. Comm.*, 1988, 1560–1562.

Cho, W. et al., "The Chemical Basis for Interfacial Activation of Monomeric Phospholipases $A_2$", *J. Biol. Chem.*, 1988, 263, 11237–11241.

Davidson, F.F. et al., "1–Stearyl,2–Stearoylaminodeoxyphosphatidylcholine, A Potent Reverisble Inhibitor of Phospholipase $A_2$", *Biochem. Biophys. Res. Comm.*, 1986, 137, 587–592.

Davidson, F.F. et al., "Inhibition of Phospholipase $A_2$ by "Lipocortins" and Calpactins", *J. Biol. Chem.*, 1987, 262, 1698–1705.

Dennis, E.A., "Phospholipases", *The Enzymes*, Boyer, P.D. (ed.), Academic Press, New York, 1983, vol. 16, 307–353.

Franson, R. et al., "Phospholipid metabolism by phagocytic cells. Phospholipase $A_2$ associated with rabbit polymorphonuclear leukocyte granules", *J. Lipid Res.*, 1974, 15, 380–388.

(List continued on next page.)

*Primary Examiner*—Jyothsna Venkat
*Assistant Examiner*—Grace Hsu
(74) *Attorney, Agent, or Firm*—Woodcock Washburn Kurtz Mackiewicz & Norris

(57) ABSTRACT

Libraries of ethylenediamine compounds having the general formula (I):

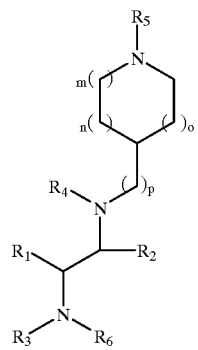

wherein R1 to R6, m, n, o and p are as defined herein, are prepared using solid phase combinatorial chemistry techniques. A heterocyclic alcohol is reacted with an ethylenediamine bound to a solid support to give a scaffold having sites of diversity. Libraries of the invention are useful for screening in biological assays in order to identify pharmaceutically useful compounds.

8 Claims, No Drawings

OTHER PUBLICATIONS

Glaser, K.B. et al., "Phospholipase $A_2$ enzymes: regulation and inhibition", *TiPS*, 1993, 14, 92–98.

Grainger, D.W. et al., "An enzyme caught in action: direct imaging of hydrolytic function and domain formation of phospholipase $A_2$ in phosphatidylcholine monolayers", *FEBS Letts.*, 1989, 252, 73–82.

Kirsanov et al., "N–Arylsulfonylethylene– and Hexamethylenediamines", *J. Gen Chem. USSR*, (Engl. Transl.), 1962, 32, 877–882.

Lombardo, D. et al., "Cobra Venom Phospholipase $A_2$ Inhibition by Manoalide", *J. Biol. Chem.*, 1985, 260, 7234–7240.

Märki, F. et al., "Differential inhibition of human secreory and cytosolic phospholipase $A_2$", *Agents Actions*, 1993, 38, 202–211.

Miyake, A. et al., "The Novel Natural Product YM–26567–1 [(+)–trans–4–(3–dodecanoyl–2,3, 6–trihydroxyphenyl)–7–hydroxy2–(4–hydroxyphenyl) chroman]: A Competitive Inhibitor of Group II Phospholipase $A_2$", *J. Pharm. Exp. Therap.*, 1992, 263, 1302–1307.

Noel, J.P. et al., "Phospholipase $A_2$ Engineering. 3. Replacement of Lysine–56 by Neutral Residues Improves Catalytic Potency Significantly, Alters Substrate Specificity, and Clarifies the Mechanism of Interfacial Recognition", *J. Am. Chem. Soc.*, 1990, 112, 3704–3706.

Oinuma, H. et al., "Synthesis and Biological Evaluation of Substituted Benzenesulfinamides as Novel Potent Membrane–Bound Phospholipase $A_2$ Inhibitors", *J. Med. Chem.*, 1991, 34, 2260–2267.

Pruzanski, W. et al., "Enzymatic Activity and Immunoreactivity of Extracellular Phospholipase $A_2$ in Inflammatory Synovial Fluids", *Inflamation*, 1992, 16, 451–457.

Sampson, B.A. et al., "Identification and Characterization of a New Gene of *Escherichia coli* K–12 Involved in Outer Membrane Permeability", *Genetics*, 1989, 122, 491–501.

Samukov, V.V. et al., "2–(4–Nitrophenyl) sulfonylethoxycarbonyl (Nse) Group as a Base–Labile α–Amino Protection for Solic Phase Peptide Synthesis", *Tetrahedron Letts.*, 1994, 35, 7821–7824.

Scott, D.L. et al., "Interfacial Catalysis: The Mechanism of Phospholipase $A_2$", *Science*, 1990, 250, 1541–1546.

Tanaka, K. et al., "A Novel Type of Phospholipase $A_2$ Inhibitor, Thielocin A1β, and Mechanism of Action", *J. Antibiotics*, 1992, 45, 1071–1078.

Verhart, C.G.J., "New base–labile amino–protective groups for peptide synthesis", *Recl. Trav. Chim. Pays–Bas*, 1988, 107, 621–626.

Vishwanath, B.S. et al., "Edema–Inducing Activity of Phospholipase $A_2$ Purified from Human Synovial Fluid and Inhibition by Aristolochic Acid", *Inflammation*, 1988, 12, 549–561.

Vojkovsky, T., "Detection of Secondary Amines on Solid Phase", *Pept. Res.*, 1995, 8(4), 236–237.

Washburn, W.N. et al., "Suicide–inhibitory Bifunctionally Linked Substrates (SIBLINKS) as Phospholipase $A_2$ Inhibitors", *J. Biol. Chem.*, 1991, 266, 5042–5048.

Wery, J.P. et al., "Structure of recombinant human rheumatoid arthritic synovial fluid phospholipase $A_2$ at 2.2 A resolution", *Nature*, 1991, 352, 79–82.

Yang, C.C. et al., "Studies on the status of lysine residues in phospholipase $A_2$ from *Naja naja atra* (Taiwan cobra) snake venom", *Biochem. J.*, 1989, 262, 855–860.

Yuan, W. et al., "Synthesis and Evaluation of Phospholipid Analogues as Inhibitors of Cobra Venom Phospholipase $A_2$", *J. Am. Chem. Soc.*, 1987, 109, 8071–8081.

* cited by examiner

ETHYLENEDIAMINE COMPOUND LIBRARIES

FIELD OF THE INVENTION

The present invention relates to diverse combinatorial libraries, processes and apparatus, in particular to diverse libraries of compounds incorporating ethylenediamine scaffolds.

BACKGROUND OF THE INVENTION

Discovery of new therapeutic compounds for treating diseases has typically involved screening individual compounds against targets representative of a particular disease of interest. The iterative process relies upon finding a compound having at least a minimal level of activity in an assay and then synthesizing as many derivatives of the lead compound as possible. The derivatives tested would form the basis of a "structure-activity relationship" (SAR) which would hopefully provide insight for designing a lead compound. Often the process is repeated time and again before any lead is uncovered. The obvious and major drawback in this drug discovery process is the generation of compounds on a one-at-a-time basis requiring much labor, time and expense.

Advances in robotics and solid-phase chemical synthesis has spawned the combinatorial approach for preparing libraries of compounds which makes synthesizing thousands of diverse compounds feasible. What once took months or even years by the traditional approach has become possible in a matter of weeks and even days through combinatorial chemistry, thereby drastically reducing the time, labor and expense involved in drug discovery.

The combinatorial approach has been adapted for preparing vast libraries of oligomeric compounds such as peptides and non-oligomeric small organic molecules on the order of $10^2$ to $10^6$ discreet compounds. Theoretically the total number of compounds in a library is limited only by the number of available reagents for forming substituents on a central scaffold.

SUMMARY OF THE INVENTION

In accordance with an aspect of the present invention there is provided a combinatorial library comprising a plurality of ethylenediamine compounds of formula (I):

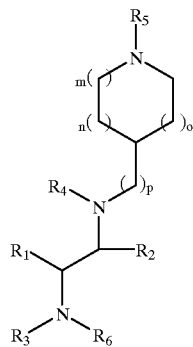

wherein:
  m is 0 or 1;
  n is 0 or 1;
  o is 1, 2 or 3 provided that m+n+o is 2 or 3;
  p is 0, 1, 2 or 3;

$R_1$ and $R_2$ are independently H or a hydrocarbyl group selected from $C_1$–$C_{10}$ alkyl, $C_2$–$C_{10}$ alkenyl, $C_2$–$C_{20}$ alkynyl, $C_6$–$C_{14}$ aryl, $C_6$–$C_{14}$ aralkyl, $C_3$–$C_{14}$ cycloalkyl, $C_5$–$C_{14}$ fused cycloalkyl, $C_4$–$C_{14}$ heterocyclyl, $C_4$–$C_{14}$ heterocycloalkyl, $C_4$–$C_{14}$ heteroaryl, $C_4$–$C_{14}$ heteroarylalkyl, and $CH(R_2)$—NH—$R_2$; wherein said hydrocarbyl group is optionally substituted with acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol or thioalkoxy;

$R_3$, $R_4$ and $R_5$ are independently H; an amino protecting group; or $CH_2$, $CH(R_2)$, $C=O$, $C=S$, $S(=O)_2$, $C(=O)NH$, $C(=S)NH$ or $C(=O)O$ substituted with H or a hydrocarbyl group selected from $C_1$–$C_{10}$ alkyl, $C_2$–$C_{10}$ alkenyl, $C_2$–$C_{20}$ alkynyl, $C_6$–$C_{14}$ aryl, $C_6$–$C_{14}$ aralkyl, $C_3$–$C_{14}$ cycloalkyl, $C_5$–$C_{14}$ fused cycloalkyl, $C_4$–$C_{14}$ heterocycle, $C_4$–$C_{14}$ heterocyclylalkyl, $C_4$–$C_{14}$ heteroaryl, $C_4$–$C_{14}$ heteroarylalkyl or $CH(R_2)$—NH—$R_2$; wherein said hydrocarbyl group is optionally substituted with oxo, acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy; and $R_6$ is H or —$R_x$—$R_y$ wherein $R_x$ is a linker and $R_y$ is a solid support.

Another aspect of the present invention, there is provided a process for preparing support bound-compounds of formula (X):

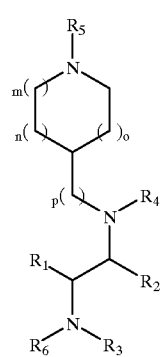

wherein $R_6$ is a solid support, comprising:
  attaching an ethylenediamine scaffold of the formula (II)

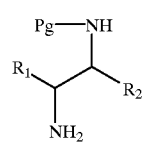

wherein Pg is an amino protecting group to a solid support via a free amino group to form a support-bound scaffold of formula (III)

III

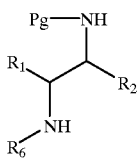

reacting the amino group of formula (III) bound to support $R_6$ with an $R_3$-building block to give a support-bound scaffold of formula (IV):

IV

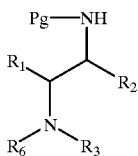

reacting the scaffold of formula (IV) with a heterocyclic alcohol of formula (V):

V

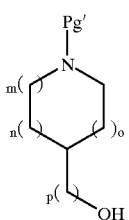

wherein Pg' is an amino protecting group to give a support-bound scaffold of formula (VI):

VI

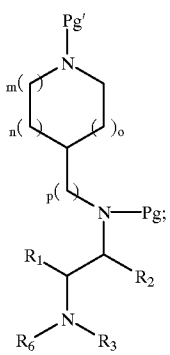

and removing one or both amino protecting groups Pg and Pg' from the scaffold of formula (VI) and reacting the deprotected amine or amines with an $R_4$- or $R_5$-building block to give a support-bound compound of formula (X).

In another aspect of the invention, there is provided a process for preparing support bound-compounds of formula (X):

X

comprising:

attaching an ethylenediamine scaffold of the formula (II)

II

to a solid support via a free amino group to form a support-bound scaffold of formula (III):

III

reacting the scaffold of formula (III) with a heterocyclic alcohol of formula (V):

V

to give a support-bound scaffold of formula (XII):

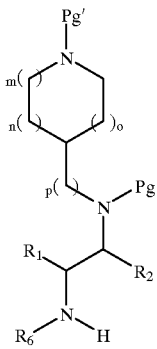

reacting the amino group of formula (XII) bound to support $R_6$ with an $R_3$-building block to give a support-bound scaffold of formula (VI):

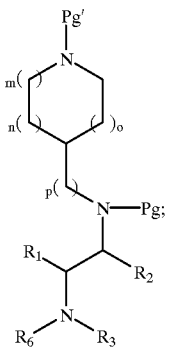

and removing one or both amino protecting groups Pg and Pg' from the scaffold of formula (VI) and reacting the deprotected amine or amines with an $R_4$- or $R_5$-building block to give a support-bound compound of formula (X).

In yet another aspect, there is provided novel compounds of formula (I) and pharmaceutical compositions thereof.

DETAILED DESCRIPTION OF THE INVENTION

The present invention provides combinatorial libraries of ethylenediamine compounds of formula (I):

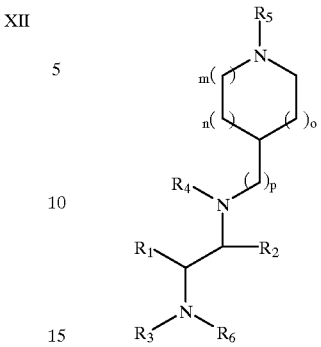

The term "library", as used herein, refers to a collection of compounds created by a combinatorial process having a common chemical structure or scaffold with one or more variable substituents, the scaffold in the present invention being an ethylenediamine. Libraries include mixtures of compounds of the invention as well as individual compounds substantially free of other related compounds arranged in arrays. In a preferred embodiment, libraries of the invention comprise at least two, three, four or five compounds of formula (I). In another preferred embodiment, libraries of the invention comprises at least ten, fifteen, twenty, fifty or one hundred compounds of formula (I).

In a preferred embodiment, substituents $R_1$ and $R_2$ are selected independently from H or a hydrocarbon chain such as $C_{1-10}$ alkyl, $C_{2-10}$ alkenyl or alkynyl, the chain being optionally substituted with a cyclic group such as a $C_{3-7}$ cycloalkyl, $C_{5-14}$ aryl, or 5–14 membered heterocycle or heteroaryl group. Included by the term "hydrocarbon chain" are straight and branched alkyl, alkenyl and alkynyl groups. By "hetero" is meant a group incorporating one or more heteroatom selected N, O and S as well as SO and $SO_2$. Said cyclic groups may be mono-, bi- or tricyclic and may themselves be substituted with substituents selected from halogen, hydroxyl, amino, carboxyl and alkyl. In a particularly preferred embodiment, both $R_1$ and $R_2$ are independently H or $C_{1-4}$ alkyl and most preferably both are H.

Substituents $R_3$, $R_4$ and $R_5$ in preferred embodiments are each independently H, an amino protecting group or a divalent group such as $CH_2$, $CH(R_2)$, C=O, C=S, $S(=O)_2$, C(=O)NH, C(=S)NH or C(=O)O substituted with H or a hydrocarbon chain as described previously for $R_3$. Again the hydrocarbon chain is optionally substituted with a cyclic group as described previously which in turn is optionally substituted with halogen, hydroxyl, amino, carboxyl and alkyl.

Preferably $R_3$ is selected from H, 2-pyrazine-carboxyl, carboxamidino, 3-(trifluoromethyl)benzoyl, carbamoyl, 2-aminopropionyl, imidizolyl-4-carboxyl, isonipecotyl, 3,5-diaminobenzoyl, isovaleryl, nalidixyl, hydroxyacetyl and thymine-1-acetyl. More preferably, $R_3$ is selected from H, 2-pyrazinyl-carbonyl, aminocarbonyl, p-tolylsulfonyl, p-nitrophenyl-carbonyl, and p-tolylaminocarbonyl.

Preferably, $R_4$ is selected from H, 2-pyrazine-carboxyl, 3,5-bis(trifluoromethyl)phenylcarbamoyl, 3-(trifluoromethyl)benzoyl, 3-pyridylmethyl, carbamoyl, aminocarbonyl, imidizole-4-carboxyl, isonipecotyl, di-t-butyl-, N-ethyl-3-carbazolylmethyl, anthraquinone-2- carbonyl, 3,5-diaminobenzoyl, isobutyl, isovaleryl, nalidixoyl, hydroxyacetyl and thymine-1-acetyl. More preferably $R_4$ is selected from H, para-t-butyl-phenylcarbonyl, p-aminophenyl-carbonyl, cyclopropyl-carbonyl, 2-hydroxyacetyl and 2-nitrophenyl-sulfonyl.

Preferably, $R_5$ is selected from H, (R)-(−)-2,2-dimethyl-5-oxo-1,3-dioxolane-4-acetyl, (S)-(+)-2,2-dimethyl-5-oxo-1,3-dioxolane-4-acetyl, carboxamidino, 2,6-dichloroisonicotinyl, carbamoylmethyl, 3-pyridylmethyl, carbamoyl, 5-hydantoinacetyl, imidazole-4-carboxyl, isonipecotyl, 2-amino-4-hydroxybutyryl, benzo[c]1,2,5-oxadiazole-5-carboxyl, 3,5-diaminobenzoyl, hydantoyl, isobutyl, nalidixoyl, niflumyl, orotyl and thymine-1-acetyl More preferably, $R_5$ is selected from H, 2-phenylacetyl, 2-hydroxyacetyl and thymine-1-acetyl.

Variables m, n, o and p are previously defined. In preferred embodiments m, n, o, and p are selected such that the heterocycle and linkage to the ethylenediamine scaffold thereby defined is selected from the group

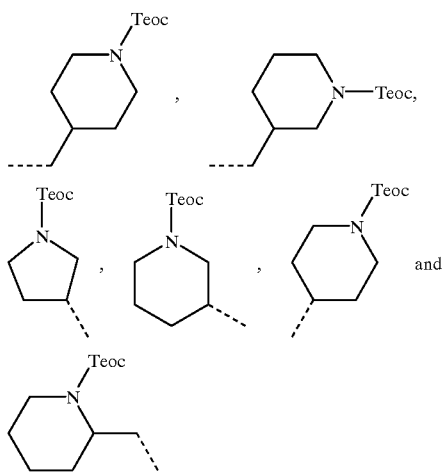

which correspond to heterocyclic alcohol reagents 5a to 5f respectively.

$R_6$ is H or a solid support. Solid supports, also called resins, according to the invention include controlled pore glass (CPG), polystyrene and cross-linked polystyrene/divinylbenzene resins, polyethylene glycol grafted polymers such as polystyrene, tentagel(R), Argogel(R), or Poros (a copolymer of polystyrene/divinylbenzene). These may be functionalized with a variety of groups including, but not limited to, hydroxy, carboxy, thio, amino, and aldehyde, for example: Wang resin, Merrifield resin, hydroxymethyl polystyrene resin, formyl polystyrene resin, aminomethyl (AM) resin, MBHA resin, Rink amide and acid resins, Seiber resin, oxime resin, trityl resin, and thiol 4-methoxytrityl resin. Particularly useful are solid supports bearing aldehyde linkers that allow for loading of amine scaffolds of this invention via reductive amination reactions. A number of commercially available supports, such as ArgoGel-MB-CHO resin, bear pendant aldehyde linkers that may be used for this purpose. Alternatively, acid stable resins such as, but not limited to, ArgoGel-OH may be derivatized with linkers such as, but not limited to, hydroxybenzaldehydes via Mitsunobu reactions so as to generate a pendant phenoxybenzaldehyde that is subsequently used for reaction with the cyclic amine scaffolds of this invention.

It will be appreciated that compounds of the invention incorporate chiral centers and therefore exist as geometric and stereoisomers. All such isomers are contemplated and are within the scope of the invention whether in pure isomeric form or in mixtures of such isomers as well as racemates.

"Amino protecting groups" are used to block reactive amino sites or amino combinatorial sites on the scaffold. Once the scaffold is attached to the solid support, the amino protecting group can be removed under basic (non-hydrolytic) conditions. The amino group is then derivatized, or functionalized, with the diverse building block or functional group of choice. This building block can be attached to the amino combinatorial site via a variety of linkages including, but not limited to, alkyl, amide, sulfonamide, carbamate, urea, aminoalkane, thiocarbamate, and thiourea. This can be accomplished by choosing the appropriate electrophile to functionalize the amino group. For example, carboxylic acids can be activated using peptide coupling reagents such as EDC, BOP or HATU and reacted with the scaffold nitrogen atom to give amides. Other reagents which can be used include, among others, acid chlorides, acid fluorides, acid imidazolides, acid anhydrides, sulfonyl chlorides, chloroformates, isocyanates, aldehydes (under reductive alkylation conditions), alkyl halides, and isothiocyanates. Thus, each time a specific linkage is desired in a library, it is introduced onto the scaffold via the appropriate coupling conditions using suitable building blocks at the amino combinatorial site.

Another feature of the present invention is the introduction of additional sites of diversity onto the scaffolds of the present invention. This may be accomplished via the use of functionalized building blocks for reaction at the amino combinatorial sites. Such building blocks include, among others, Fmoc-amino acids where the amino group of the amino acid building block is selectively protected with a labile protecting group, such as Fmoc. The carboxylic group of the amino acid building block reacts with the amino combinatorial site on the scaffolds of this invention. The products so generated may be further combinatorialized via deprotection of the Fmoc group on the pendant amino group derived from the previously used amino acid building block and reaction of this amine with additional building blocks as described below. Monocyclic, bicyclic and oligomeric amine libraries of this invention may therefore bear two or more sites of diversity based on the selective protection and deprotection of functional groups including amines and alcohols on the scaffolds and based on the building blocks used.

Amino protecting groups stable to acid treatment are selectively removed with base treatment, and are used to make reactive amino groups selectively available for substitution. Examples of such groups are the FMOC (E. Atherton and R. C. Sheppard in *The Peptides*, S. Udenfriend, J. Meienhofer, Eds., Academic Press, Orlando, 1987, volume 9, p.1), and various substituted sulfonylethyl carbamates exemplified by the Nsc group (Samukov et al., *Tetrahedron Lett*, 1994, 35:7821; Verhart and Tesser, *Rec. Trav. Chim. Pays-Bas*, 1987, 107:621). Additional amino protecting groups include but are not limited to, carbamate protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl.

In a particular aspect of the invention there are provided processes for preparing compounds of formula (I). In a first general method an ethylene diamine scaffold of formula (II) with a free amino group and a protected amino group (Pg) is attached to a solid support. The amino group attached to the solid support is functionalized by reacting the scaffold with an $R_3$-building block to give a support-bound scaffold of formula (IV). This scaffold is reacted with an N-protected (Pg') heterocyclic alcohol of formula (V) to give a support-bound scaffold of formula (VI). The Pg protecting group may then be removed leaving an unmasked amino group which can be functionalized with an $R_4$-building block. Once derivatived, the Pg' amino protecting group on the heterocycle may be removed unmasking the amine which is functionalized with an $R_5$-building block. Finally, the fully functionalized scaffold can be cleaved from the solid support and collected. A particular embodiment of this method is illustrated in scheme 1 below.

In an alternative method, the ethylene diamine scaffold of formula (III) is first reacted with a heterocyclic alcohol of formula (V) and then functionalized with an $R_3$-building block. Subsequent deprotection and functionalizing steps are the same as in the previous method. A particular embodiment of this alternative method is illustrated in scheme 2 below.

By "building block" is meant a reagent for derivatizing or functionalizing the scaffold of the invention. Suitable building blocks include sulfonyl halides, triphosgene, isocyanates, isothiocyanates, acid halides, carboxylic acids, aryl halides, alkyl halides, aldehydes, ketones and activated guanylating agents. Preferred $R_3$-building blocks are selected from carboxylic acids, acid halides, sulfonyl halides and isocyanates and $R_4$- and $R_5$-building blocks are preferably selected from aldehydes, ketones, alkyl halides, aryl halides, carboxylic acids, acid halides, sulfonyl halides, isocyantes and activating guanylating agents.

More prefered $R_3$-building blocks are selected from 2-pyrazinecarboxylic acid, 3,5-bis(trifluoromethyl)phenyl isocyanate, 3-(trifluoromethyl)benzoic, acid, 4-methoxybenzyl isocyanate, BOC-beta-ALA-OH, BOC-imidazole-4-carboxylic acid, BOC-isonipecotic acid, bis(BOC-3,5-diaminobenzoic acid), isovaleric acid, nalidixic acid, t-butoxyacetic acid, and thymine-1-acetic acid More prefered $R_4$-building blocks are selected from 2-pyrazinecarboxylic acid, 3,5-bis(trifluoromethyl)phenyl isocyanate, 3-(trifluoromethyl)benzoic acid, 3-pyridinecarboxaldehyde, 4-methoxybenzyl isocyanate, BOC-imidazole-4-carboxylic acid, BOC-isonipecotic acid, Di-tert-butyl dicarbonate, N-ethyl-3-carbazolecarboxaldehyde, anthraquinone-2-carboxylic acid, bis(BOC-3,5-diaminobenzoic acid), isobutyraldehyde, isovaleric acid, nalidixic acid, t-butoxyacetic acid, and thymine-1-acetic acid.

More prefered $R_5$-building blocks are selected from (R)-(−)-2,2-dimethyl-5-oxo-1,3-dioxolane-4-acetic acid, (S)-(+)-2,2-dimethyl-5-oxo-1,3-dioxolane-4-acetic acid, 1H-pyrazole-1-carboxamidine-HCl, 2,6-dichloroisonicotinic acid, 2-bromoacetamide, 3-pyridinecarboxaldehyde, 4-methoxybenzyl isocyanate, 5-hydantoinacetic acid, BOC-imidazole-4-carboxylic acid, BOC-isonipecotic acid, N-BOC-L-homoserine, benzofurazan-5-carboxylic acid, bis(BOC-3,5-diaminobenzoic acid), hydantoic acid, isobutyraldehyde, nalidixic acid, niflumic acid, orotic acid, and thymine-1-acetic acid.

Scheme 1

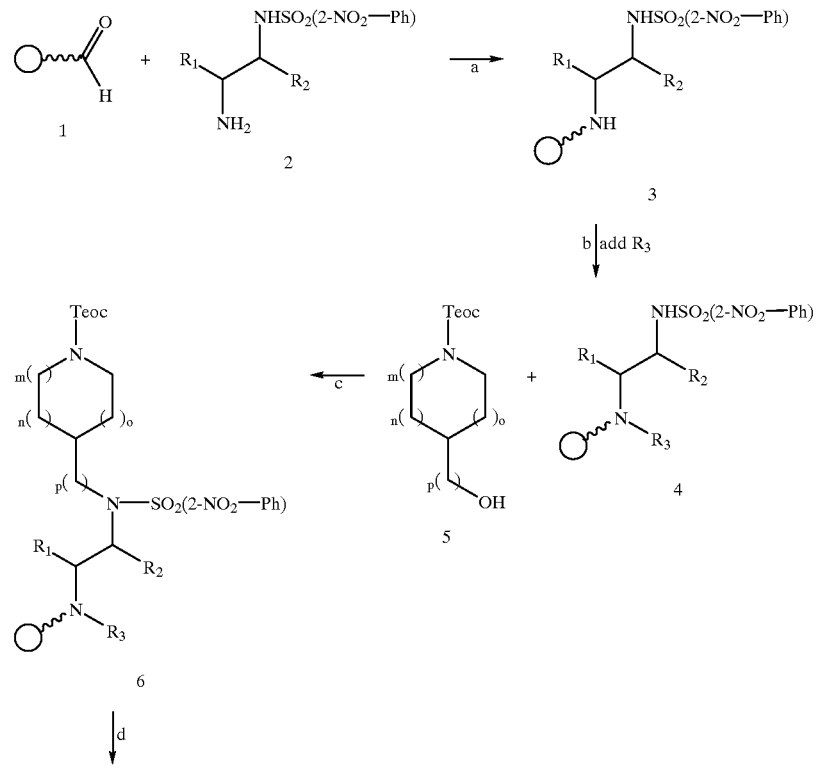

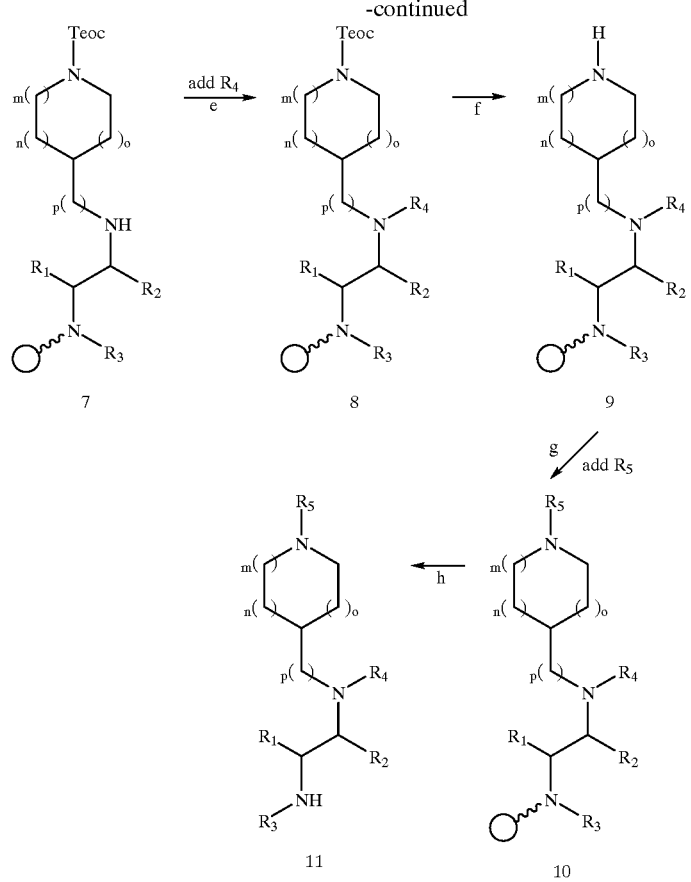
Scheme 2
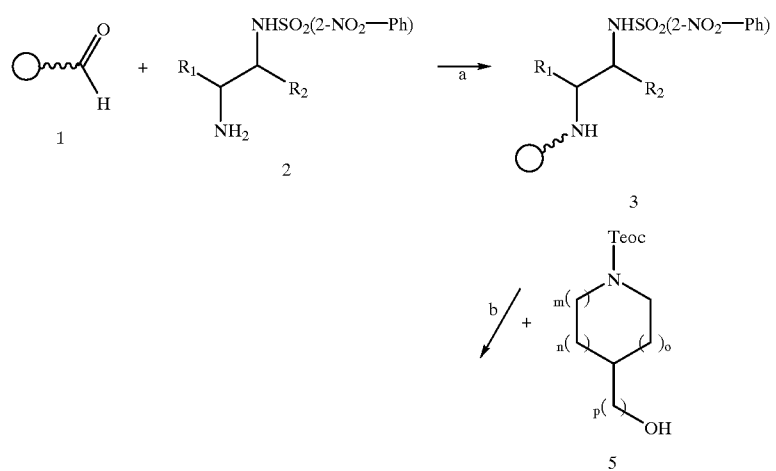

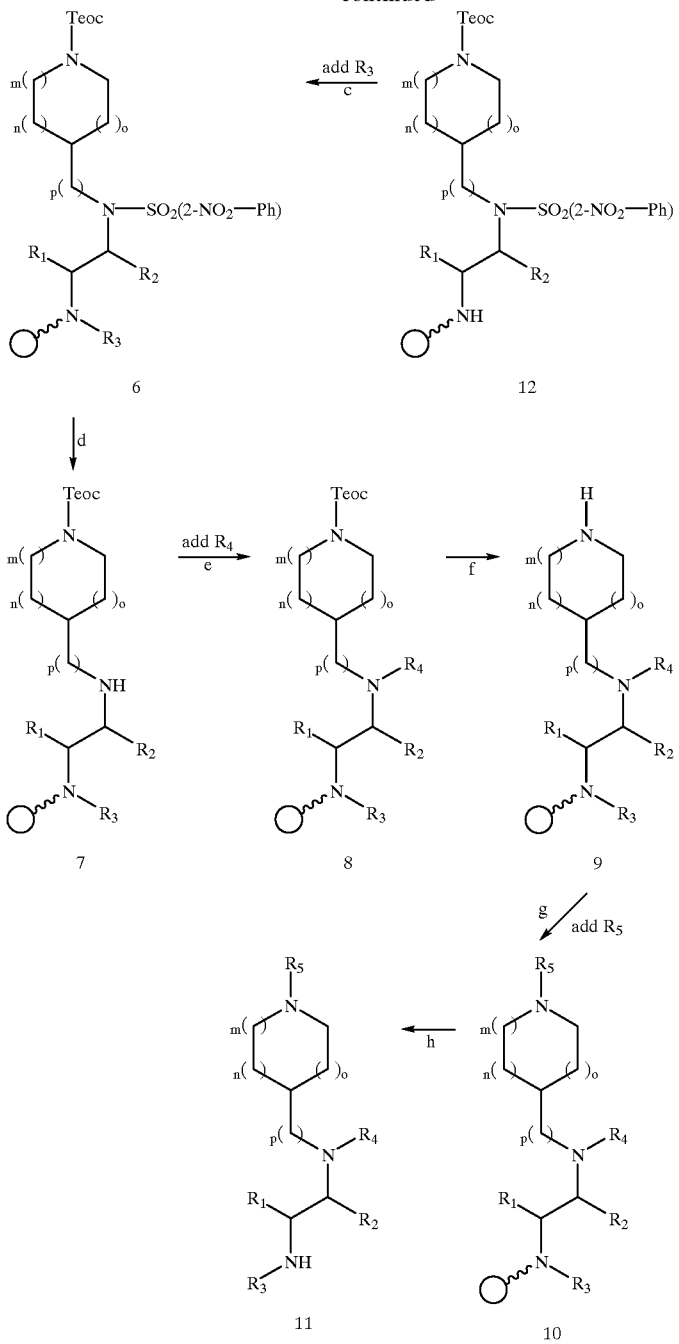

Referring to particular embodiments of schemes 1 and 2 the following procedures may be employed.

Attachment to Resin

To the appropriate resin containing a benzaldehyde linker (preferably ArgoGel-MB-CHO resin purchased from Argonaut Technologies) is added a solution of the appropriately protected nitrobenzenesulfonyl-protected diamine scaffold in 4:1 MeOH/CH(OMe)$_3$ (1.15 mmole scaffold/mmole resin functionality in 5 mL/gram dry resin solvent). The mixture is gently shaken for 15 h, then a solution of BH3-pyridine (2 mmole/mmole resin functionality) and acetic acid (2 mmole/mmole resin functionality) in 4:1 MeOH/CH(OMe)$_3$ (0.5 mL/gram dry resin solvent) is added. The suspension is gently shaken (gas evolution occurs) for 3 h at rt, then filtered, and washed with MeOH (3×), CH$_2$Cl$_2$ (3×), DMF (3×) and CH$_2$Cl$_2$ (3×) and dried with a flow of inert gas to provide resins of type 3.

Attachment of Heterocyclic Alcohol and Functionalization

To the appropriate resin 3 is added triphenylphosphine (TPP) (6 mmole/mmole resin functionality) in CH$_2$Cl$_2$ (5 mL/gram dry resin). A solution of the appropriate alcohol 5 (6 mmole/mmole resin functionality) in CH$_2$Cl$_2$ (5 mL/gram dry resin) is added, and the reaction mixture cooled in an ice bath. Diisopropylazodicarboxylate (6 mmole/mmole resin functionality) is then added dropwise slowly with gentle agitation. The ice bath is removed after addition, and the mixture gently agitated for 24 h. The resin 12 is then washed with CH$_2$Cl$_2$ (3×), DMF (3×) and CH$_2$Cl$_2$ (3×) and dried with a flow of inert gas.

The resin bound scaffold 12 can be functionalized at the first open position (R$_3$) as a sulfonamide, urea, or amide with an appropriate electrophile R$_3$-building block as described previously to provid resin 6.

Removal of 2-Nitrobenzenesulfonyl Protecting Group and Functionalization

The resin bound scaffold 6 is treated with a 0.5 M solution of 2-mercaptoacetic acid in NMP (25 mL/mmole scaffold) containing 1 M DBU for 1 h, then washed with DMF (3×) and CH$_2$Cl$_2$ (3×) and dried with a flow of inert gas to provide 7. The resin bound scaffold 7 is functionalized at the corresponding open position (R$_4$) as a sulfonamide, urea, amide, aryl amine, or alkyl amine with an appropriate electrophile R$_4$-building block as described previously to provide resin 8.

Removal of Teoc Protecting Group and Functionalization

To the appropriate resin bound scaffold 8 is added a 0.2 M solution (25 mL/mmole scaffold) solution of TBAF in NMP. The suspension is allowed to stand for 1 h at rt, then filtered, and washed with DMF (3×) and CH$_2$Cl$_2$ (3×) and dried with a flow of inert gas to provide 9. The resin bound scaffold 9 is functionalized at the corresponding open position (R$_5$) as a sulfonamide, urea, amide, alkyl amine, or aryl amine with an appropriate electrophile R$_5$-building block as described previously to provide resin 10.

Cleavage from Support

To the resin bound functionalized scaffold 10 is added TFA containing 2.5% Et$_3$SiH (25 mL/mmole scaffold), and the suspension is allowed to stand for 4 h at rt. The mixture is filtered, the resin washed with TFA (3×10 mL/mmole scaffold), and the combined filtrates concentrated under reduced pressure, then dried over KOH at 0.1 mm Hg to provide the appropriate compound or mixture of compounds of general formula 11.

General procedures for functionalizing with building blocks is described as follows.

Sulfonylation of Nitrogen

To the appropriate resin bound scaffold is added a 0.1 M solution (25 mL/mmole scaffold) solution of the appropriate sulfonyl chloride in 4:1 NMP/CH$_2$Cl$_2$ containing 0.15 M DIEA. The suspension is allowed to stand for 3 h at rt, then filtered, and washed with DMF (3×) and CH$_2$Cl$_2$ (3×) and dried with a flow of inert gas.

Urea Formation at Nitrogen From Isocyanates

To the appropriate resin bound scaffold is added a 5 0.15 M solution (25 mL/mmole scaffold) of the appropriate isocyanate in NMP. The suspension is allowed to stand for 3 h at rt, then filtered, and washed with DMF (3×) and CH$_2$Cl$_2$ (3×) and dried with a flow of inert gas.

Urea Formation at Nitrogen From Amines

To the appropriate resin bound scaffold is added a 0.06 M solution (5 mL/g of dry resin) of triphosgene in CH$_2$Cl$_2$, followed by a 0.18 M solution (5 mL/g of dry resin) of DIEA in CH$_2$Cl$_2$. The suspension was allowed to stand for 0.25 h, and 0.2 M solution of an appropriate amine (10 mL/g) in NMP is added. The suspension is allowed to stand for 2.5 h at rt, then filtered, and washed with DMF (3×) and CH$_2$Cl$_2$ (3×) and dried with a flow of inert gas.

Thiourea Formation at Nitrogen From Isothiocyanates

To the appropriate resin bound scaffold is added a 0.15 M solution (25 mL/mmole scaffold) of the appropriate isothiocyanate in NMP. The suspension is allowed to stand for 3 h at rt, then filtered, and washed with DMF (3×) and CH$_2$Cl$_2$ (3×) and dried with a flow of inert gas.

Thiourea Formation at Nitrogen From Amines

To the appropriate resin bound scaffold is added a 0.18 M solution (5 mL/g of dry resin) of thiophosgene in CH$_2$Cl$_2$, followed by a 0.18 M solution (5 mL/g of dry resin) of DIEA in CH$_2$Cl$_2$. The suspension was allowed to stand for 0.25 h, and 0.2 M solution of an appropriate amine (10 mL/g) in NMP is added. The suspension is allowed to stand for 2.5 h at rt, then filtered, and washed with DMF (3×) and CH$_2$Cl$_2$ (3×) and dried with a flow of inert gas.

Acylation at Nitrogen with Acyl Halides

To the appropriate resin bound scaffold is added a 0.10 M solution (25 mL/mmole scaffold) of the appropriate acid halide in 1:1 pyridine/CH$_2$Cl$_2$. The suspension is allowed to stand for 3 h at rt, then filtered, and washed with DMF (3×) and CH$_2$Cl$_2$ (3×) and dried with a flow of inert gas.

Acylation at Nitrogen with Carboxylic Acids

To the appropriate resin bound scaffold is added a 0.20 M solution (5 mL/g of dry resin) of the appropriate carboxylic acid in 1:1 NMP/CH$_2$Cl$_2$. A 1.0 M solution of DIEA in CH$_2$Cl$_2$ (2 mL/g of dry resin) is added, followed by a 0.33 M solution of O-(7-azabenzotriazol-1-yl)-1,1,3,3-tetramethyluronium hexafluorophosphate (HATU) in NMP (3 mL/g of dry resin). The suspension is allowed to stand for 3 h at rt, then filtered, and washed with CH$_2$Cl$_2$ (3×), DMF (3×), CH$_2$Cl$_2$ (3×) and dried with a flow of inert gas.

Alkylation at Nitrogen with Alkyl Halides

To the appropriate resin bound scaffold is added a 0.10 M solution (25 mL/mmole scaffold) of the appropriate alkyl halide in 10:1 NMP/DIEA. The suspension is allowed to stand for 3 h at rt, then filtered, and washed with DMF (3×) and CH$_2$Cl$_2$ (3×) and dried with a flow of inert gas.

Alkylation at Nitrogen with Aldehydes or Ketones

To the appropriate resin bound scaffold is added a 0.20 M solution (5 mL/g of dry resin) of the appropriate carbonyl compound in 4:1 MeOH/CH(OMe)$_3$, followed by a freshly prepared 1.0 M solution (1 mL/g of dry resin) of BH3.pyridine complex in 4:1 MeOH/CH(OMe)$_3$ containing 6% v/v acetic acid. The suspension is allowed to stand for 3 h at rt, then filtered, and washed with CH$_2$Cl$_2$ (3×), DMF (3×), CH$_2$Cl$_2$ (3×) and dried with a flow of inert gas.

Protection of Nitrogen

To the appropriate resin bound scaffold is added a 0.2 M solution (25 mL/mmole scaffold) of di-tert-butyldicarbonate in NMP. The suspension is allowed to stand for 3 h at rt, then filtered, and washed with DMF (3×) and CH$_2$Cl$_2$ (3×) and dried with a flow of inert gas.

The processes for preparing ethylenediamine compounds of the present invention may be carried out in any vessel capable of holding the liquid reaction medium. In one embodiment, the process of the invention is carried out in containers adaptable to parallel array synthesis. In particular, the ethylenediamine library of the invention can be formed in a 96-well plate and typically in a two-dimensional array of defined reservoirs, wherein an ethylenediamine compound of formula (I) is prepared in each reservior. Thus the library comprises a plurality of reservoir arrays e.g. well plates, each well containing a discreet compound or mixture of compounds. Following simultaneous preparation of the library compounds in the array, the compounds can be transferred in whole or in part to other reservoir arrays to prepare multiple copies of the library apparatus or to subject the library to additional reactions or biological assays. Copies of the library apparatus (daughter well plates, each comprising a 2-dimensional array of defined reservoirs with each reservoir containing a predetermined reaction product of the library) are useful as replaceable elements in automated assay machines. The apparatus allows convenient access to a wide variety of ethylenediamine compounds. A preferred reservoir array for use in making the library is a multi-well titer plate, typically a 96-well microtiter plate. Upon completion, reaction products may be analyzed by mass spectrometry and nuclear magnetic resonance spectrometry.

In an aspect of the invention there is provided assay kits for the identification of pharmaceutical lead compounds. The assay kit comprises as essential parts a well plate apparatus containing an array of ethylenediamine compounds of the invention (discreet compounds or mixtures thereof) and biological assay materials. The biological assay materials employed will be those predictive of success for an associated disease state. Illustrative biological materials useful in the kit of the invention are those required to perform the following assays:

in vitro assays enzymatic inhibition receptor-ligand binding protein-protein interaction protein-DNA interaction cell based functional assays transcriptional regulation signal transduction/second messenger viral infectivity incubate and read assays scintillation proximity assays angiotensin II IPA receptor bidning assay endothelia convertin enzym $^{125}$I SPA assay HIV proteinase $^{125}$I SPA enzyme assay cholesteryl ester transfer (CETP) $^3$H SPA assay fluorescence correlation spectroscopy colorimeric biosensors $Ca^{2+}$ EGTA for cell-based assays receptor gene constructs for cell based assays lucerferase, green fluorescent protein, beta-lactamase electrical cell impedance sensor assays.

EXAMPLE 1

Synthesis of Teoc Protected Heterocyclic Alcohols 5a–5f

N-Teoc-4-hydroxymethylpiperidine (5a)

In a 1L round bottomed flask isonipecotic acid (50.00 g, 0.39 moles, Aldrich) was dissolved in 500 mL of 1:1 acetonitrile:water. To this solution was added triethylamine (81 mL, 58.75 g, 0.58 moles) followed by TEOC-NHS (trimethylsilyl ethyloxycarbonyl-NHS) (113.0 g, 0.47 moles) and the reaction stirred overnight at room temperature. The solution was then concentrated to one half volume and poured into 1M HCl and extracted with dichloromethane (DCM) three times. The organic solutions were combined and washed with brine, and then dried with magnesium sulfate. The filtrate was concentrated under vacuum and dried overnight under high vacuum to give 105 g of white crystalline N-Teoc-isonipecotic acid. A 2 L round bottomed flask was charged with N-Teoc-isonipecotic acid (60.0 g, 0.22 moles), dissolved in 1 L of THF and cooled to 0 C. To this solution was added borane:dimethyl sulfide (10.0 M, 44 ml, 0.44 moles) dropwise over 30 minutes. The reaction was then heated to reflux for 2 hours. At the end of the time the reaction was quenched with methanol, added in small portions until the evolution of gases stopped. The solution was cooled to room temperature and evaporated to one third volume and poured into brine. The solution was extracted three times with dichloromethane, the extracts combined, dried over magnesium sulfate, and concentrated to a clear oil weighing 54.86 g, 96% yield: $^1$H (CDCl$_3$): 4.0 (t, 4 H); 3.3 (d, 3 H); 2.6 (t, 2 H); 1.6 (m, 3 H); 1.0 (m, 5 H); 0.9 (s, 9 H); $^{13}$C (CDCl$_3$): 155.5, 66.8, 63.2, 43.5, 38.4, 28.4, 17.4, −1.7; FAB MS (M+H) observed 260.1671 calculated 260.1682.

N-Teoc-3-hydroxymethyl Piperidine (5b)

In a 1L round bottomed flask 3-hydroxymethyl piperidine (33.5 mL, 24.30 g, 0.24 moles) was dissolved in 500 mL of 1:1 acetonitrile:water. To this solution was added triethylamine (33.5 mL, 24.30 g, 0.24 moles) followed by TEOC-NHS (61.9 g, 0.24 moles) and the reaction stirred overnight at room temperature. The solution was then concentrated to one half volume and poured into 1M HCl and extracted with dichloromethane three times. The organic solutions were combined and washed with brine to give 56.89 g of product 5b as a clear oil; $^1$H (CDCl$_3$): 3.9 (t, 2 H); 3.9 (m, 1 H); 3.4 (d, 3 H); 3.7 (m, 2 H); 2.6 (m, 3 H); 1.3 (m, 2 H); 0.9 (t, 2 H); 0.0 (s, 9 H); $^{13}$C (CDCl$_3$): 155.7, 64.4, 63.2, 46.6, 44.3, 38.1, 26.8, 24,0, 17.5, −1.7; FAB MS (M+H) observed 260.1690 calculated 260.1682.

N-Teoc-3-hydroxypyrrolidine (5c).

This compound was prepared according to the procedures for intermediate 5b using the corresponding alcohol 3-hydroxy-pyrrolidine.

N-Teoc-3-hydroxypiperidine (5d)

Following the procedure for intermediate 5b, 3-hydroxypiperidine (20.00 g, 0.20 moles) was treated with triethylamine (30 ml, 22.6 g, 0.22 moles) and Teoc-NHS (56.4 g, 0.22 moles). After workup and concentration 50.3 g of a clear oil was isolated representing a quantitative yield; $^1$H (CDCl$_3$): 4.1 (t, 2 H); 3.8 (m, 2 H); 3.5 (m, 2 H); 2.8 (m, 2 H); 1.8 (m, 1 H); 1.6 (m, 1 H); 1.4 (m, 2 H); 0.9 (t, 2 H); 0.0 (s, 9 H); $^{13}$C (CDCl$_3$): 155.7, 65.6, 63.3, 50.3, 43.6, 32.3, 22.5, 17.4, −1.7; FAB MS (M+H) observed 246.1515 calculated 246.1525.

N-Teoc-4-hydroxypiperidine (5e)

This compound was prepared according to the procedures for intermediate 5b using the corresponding alcohol 4-hydroxy-piperidine.

N-Teoc-2-hydroxymethyl Piperidine (5f)

Following the procedure for intermediate 5b, 2-hydroxymethyl piperidine (25.0 g, 0.22 moles) was treated with triethylamine (33.5 mL, 24.30 g, 0.24 moles) and Teoc-NHS (62.00 g, 0.22 moles). The resulting organic solutions were combined, washed with brine and then dried with magnesium sulfate. The filtrate was concentrated under vacuum and dried overnight under high vacuum to give 56.98 g of product 5f representing a quantitative yield; 1H (CDCl3): $^1$H (CDCl$_3$) : 4.2–3.8 (m, 4 H); 3.6 (m, 2 H); 3.2 (s, 1 H); 2.8 (t, 1 H); 1.7–1.2 (m, 6 H); 0.9 (t, 2 H); 0.0 (s, 9 H); $^{13}$C (CDCl$_3$) : 156.5, 63.3, 60.5, 52.1, 39.6, 25.0, 24.7, 19.1, 17.4, −1.7; FAB MS (M+H) observed 260.1682 calculated 260.1682.

EXAMPLE 2

Preparation of N-o-nitrophenylsulfonylethylene-diamine Derivatized Resin 3'

To ArgoGel-MBCHO resin 1 (Argonaut Technologies Inc., San Carlos, Calif.) (5.0 g, 2.0 mmol, 0.4 mmol/g) was added MeOH (20 mL), trimethyl orthoformate (5 mL), N-o-nitrophenylsulfonylethylene-diamine 2' (0.65 g, 2.3 mmol, 2.3 equiv.) prepared according to the procedures described in Kirsanov et al (J. Gen. Chem. USSR (Engl. Transl.), 1962, 32:877–882) and diisopropylethylamine (DIEA) (0.4 mL, 2.3 mmol, 2.3 equiv). The reaction was left swirling on an orbtital shaker, overnight. The following day the reaction was placed under argon and borane-pyridine complex (8M, 0.75 mL, 6 mmol, 3 equiv) was added followed by acetic acid (0.35 mL, 6 mmol, 3 equiv.). The mixture was left swirling on orbital shaker under argon, overnight. The following day the resin was filtered and washed with MeOH (3×20 mL), DMF (3×20 mL), DCM (3×20 mL), and MeOH (3×20 mL). The resin was then dried over $P_2O_5$, under high vacuum to give 5.23 g of the ethylenediamine resin 3' (97%) yield based on initial resin substitution. The purity of resin 3a was assessed to be >95% by $^{13}$C gel phase NMR spectroscopy: $^{13}$C NMR ($C_6D_6$) δ (peak frequencies not off-scale) 160.36, 159.02, 148.45, 133.51, 132.47, 131.41, 124.96, 105.277, 99.59, 70.09, 67.96, 55.30, 47.44, 42.24.

EXAMPLE 3

Manual Library Preparation—method 1

Sulfonylation of the Secondary Amine of Resin 1

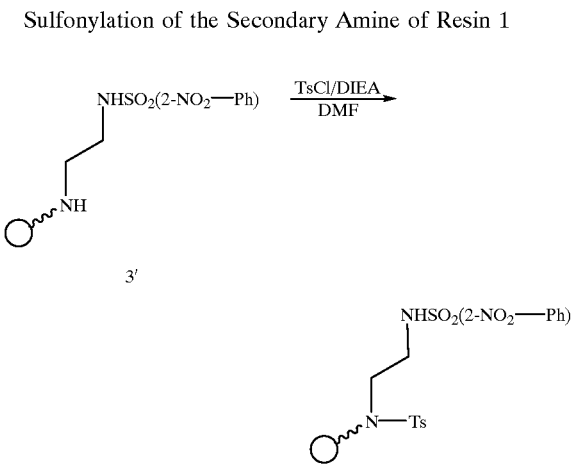

To resin 3' (1.0 g, 0.37 mmol/g theoretical resin substitution, 3.7×10$^{-4}$ mol) was added a solution of p-toluenesulfonyl chloride (0.17 g, 0.90 mmol, 2.4 equiv) and diisopropylethylamine (0.57 mL, 0.90 mmol, 2.4 equiv) in DCM (7 mL). The reaction was left swirling on an orbital shaker, overnight. The next day the resin was filtered and washed with DCM (5×10 mL), DMF (5×10 mL), MeOH (5×10 mL), DMF (5×10 mL) and MeOH (5×10 mL). According to a secondary amine resin test desribed by Vojkovsky T. (Pept. Res., 1995, 8:236), the reaction had gone to completion. Resin 4' was then dried over $P_2O_5$, under high vacuum to 1.0 g (94% yield based on theoretical resin substitution). A portion of resin 4' (35 mg) was subjected to 95% TFA/5% $H_2O$ cleavage for 1.5 h. The resin was then filtered and the filtrate evaporated in vacuo to give resin-free compound 4' (4.2 mg, 84% mass recovery) which was characterized by mass spectrometry and its purity assessed by HPLC analysis: HRMS (FAB+) Expected M+H 400.0637. Observed 400.0637; RP-HPLC: RT=19.21 (one peak, 100%), by evaporative light scattering detector (SEDEX).

Mitsunobu Reaction with Resin 4'

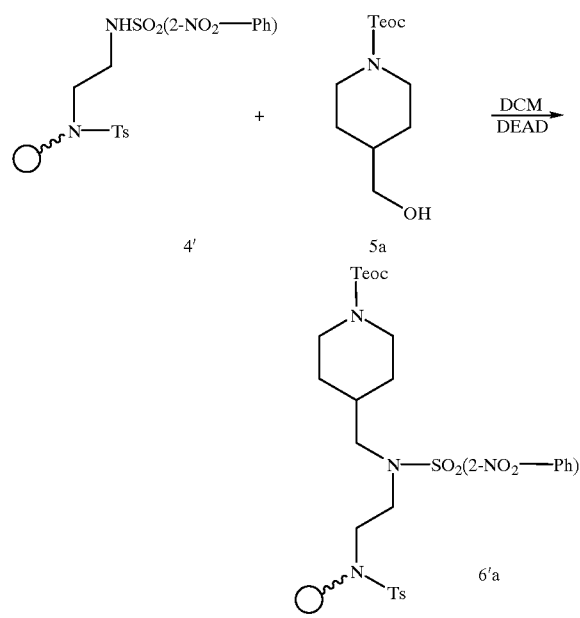

Prior to the Mitsunobu reaction, resin 4', triphenylphosphine and the glassware were dried under high vacuum, over $P_2O_5$. The resin (0.15 g, 5.25×10$^{-5}$ mol) was first swelled in DCM (1.5 mL), under argon. A solution of triphenylphosphine (59 mg, 2.25×10$^{-4}$ mol, 4.3 equiv) in DCM (0.2 mL) was then added to the resin followed by a solution of N-teoc-4-(hydroxymethyl)-piperidine 5a (58 mg, 2.25×10$^{-4}$ mol, 4.3 equiv) in DCM (0.2 mL). The reaction was then stirred with a stirring bar and DEAD (35 μL, 2.25×10$^{-4}$ mol, 4.3 equiv) dissolved in DCM (0.2 mL) was added slowly over 5 min. After the addition the stirring was stopped and the reaction was left to sit under argon, overnight. The next day the resin was filtered and washed with DCM (5×5 mL), DMF (5×5 mL), and MeOH (5×5 mL). Resin 6'a was dried over $P_2O_5$, under high vacuum to give 1.57 g (96% yield based on theoretical resin substitution). A portion of resin 6'a (45 mg) was cleaved with 95% TFA/5% $H_2O$ for 1.5 h to give resin-free 6'a (9 mg, quantitative mass recovery based on the TFA salt) after removing the volatiles of the filtrate in vacuo. Resin-free 6'a was characterized by mass spectrometry and its purity assessed by HPLC analysis: HRMS (FAB+) Expected M+H 497.1529. Observed 497.1515; RP-HPLC: RT=13.3 min (91%, one peak).

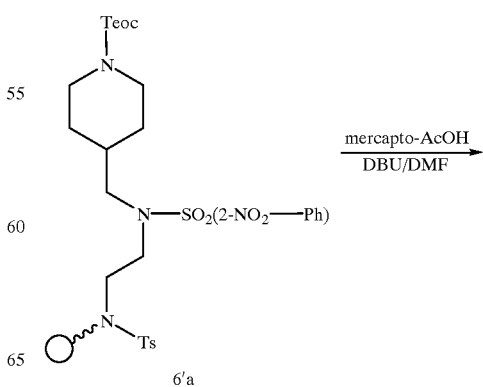

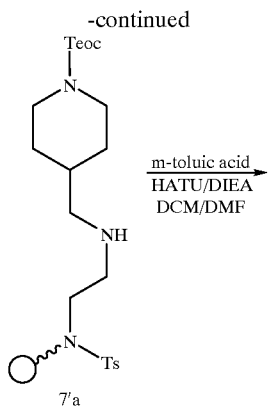

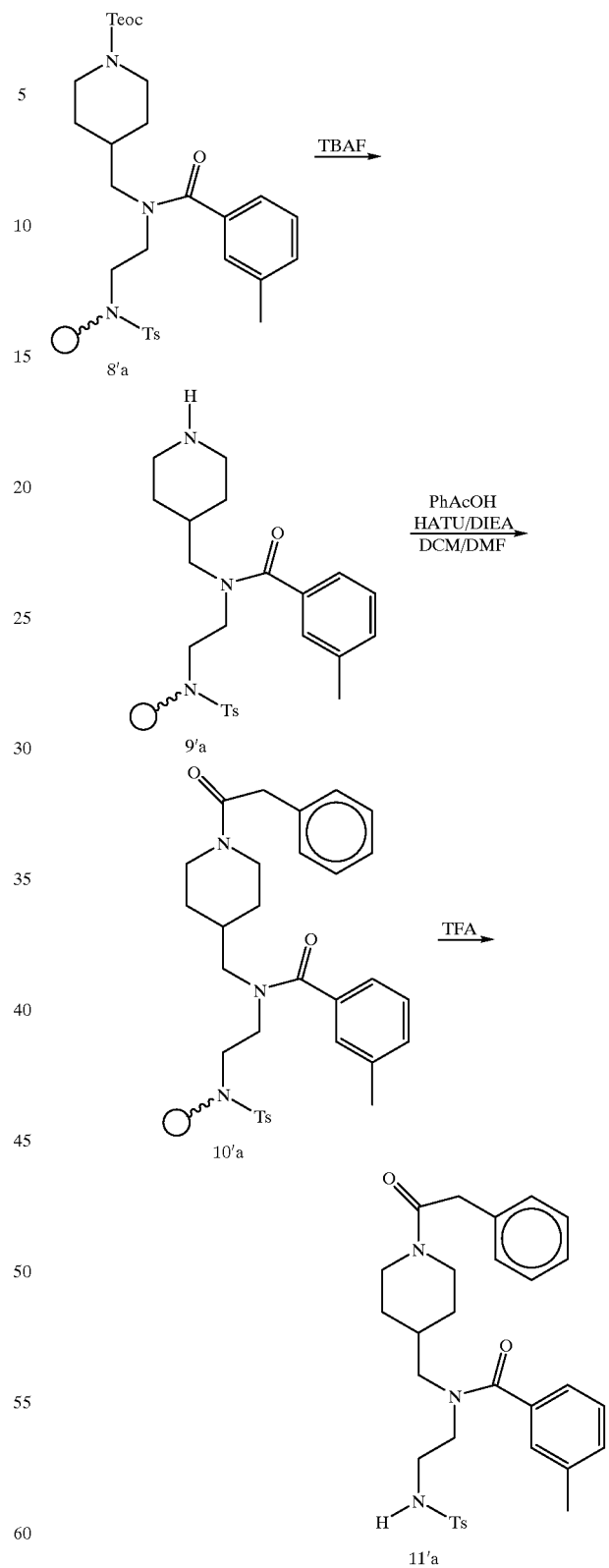

o-Nitrophenylsulfonyl-deprotection of Resin 6'a and Functionalization with m-toluic Acid The o-nitrobenzenesulfonyl group was removed by treating resin 6'a (0.48 g, 1.54 mol) with a 10 mL solution of 0.5M mercaptoacetic acid/1M DBU solution in DMF to give resin 7'a. The reaction was left swirling on an orbital shaker for 30 min. According to the secondary amine resin test, complete deprotection had taken place. The resin was then filtered and washed with DMF (3×10 mL), DCM (3×10 mL), MeOH (3×10 mL), and DMF (3×10 mL). To resin 7'a was then added a 10 mL of a solution of m-toluic acid (0.1 g, 0.77 mmol, 5 equiv), HATU (0.29 g, 0.77 mmol, 5 equiv) and DIEA (0.27 mL, 1.54 mmol, 10 equiv) in DCM/DMF (1:1) to give resin 8'a. The reaction was allowed to proceed overnight, on a shaker. According to the secondary amine resin test, the reaction had gone to completion. The resin was then filtered and washed with DMF (3×10 mL), DCM (3×10 mL) and MeOH (3×10 mL). Resin 8'a was dried over $P_2O_5$, under high vacuum, to 0.47 g (89% yield). A portion of resin 8'a (76 mg) was cleaved with 95% TFA/5% $H_2O$ for 1.5 h to give resin-free compound 8'a (11.4 mg, 85% mass recovery based on the TFA salt) after removing the volatiles of the filtrate in vacuo. Resin-free 8'a was characterized by mass spectrometry and its purity assessed by HPLC analysis: HRMS (FAB+) Expected M+H 430.2164. Observed 430.2166.; RP-HPLC: RT=14.6 min (96%, one peak).

Teoc-deprotection of Resin 8'a, Functionalization with Phenylacetic Acid and Cleavage from Support Resin 8'a (0.39 g, $1.28\times10^{-4}$ mmol) was then treated with 5 mL of 0.2M TBAF in THF for 1 h to give the resin 9'a. According to the secondary amine resin test, the deprotection was complete. The resin was then filtered and washed with DMF (3×10 mL), DCM (3×10 mL), MeOH (3×10 mL), and DMF (3×10 mL). To resin 9'a was added 10 mL of a solution of phenylacetic acid (80 mg, 5.9×10$^{-4}$ mol, 4.6 equiv) HATU (0.22 g, 5.8×10$^{-4}$ mol, 4.6 equiv) and DIEA (0.20 mL, 1.15×10$^{-3}$ mol, 9 equiv) in DCM/DMF (1:1) to give resin 10'a. The reaction was allowed to proceed overnight, on a shaker. The next day, according to the secondary amine resin test, the reaction had gone to completion. The resin was then filtered and washed with DMF (3×10 mL), DCM (3×10 mL) and MeOH (3×10 mL). The resin was dried over $P_2O_5$, under high vacuum to provide 0.35 g of 10'a (92% yield). A portion of resin 10'a (115 mg) was cleaved with 95% TFA/5% $H_2O$ for 1.5 h to give compound 11'a (16.8 mg, 81% mass recovery) after removing the volatiles of the filtrate in vacuo. Compound 11'a was characterized by mass spectrometry and its purity assessed by HPLC analysis: HRMS(FAB+) Expected M+H 547.2583. Observed 548.2569; RP-HPLC: RT=21.25 (94%, one peak).

EXAMPLE 4

Automated Library Preparation—method 1

Resin 3 was prepared manually in bulk, then loaded into a 96 well reaction vessel and loaded onto a parallel array synthesizer as described in Brennan et al (Biotechnol Bioeng, 1998, 61(1):33–45). The synthesizer was then loaded with the following command file input (saved as a tab-delimited text file):

```
INITIAL_WASH
BEGIN
    Repeat 3
    Add   DCM   300
    Drain 20
    End_Repeat
END
FUNCTIONALIZE_R1
BEGIN
    Next_Sequence
    Prime         <SEQ>
    Prime         <ACT1>
    Prime         <ACT2>
    Repeat   6
    Prime         <SEQ>
    Prime         <ACT1>
    Prime         <ACT2>
        Add   <SEQ>100+<ACT1>100
        Wait 1800
        Drain20
    End_Repeat
    Repeat     5
        Add DCM   300
        Drain20
    End_Repeat
        Repeat5
        Add   DMF200
        Drain20
    End_Repeat
    Repeat     8
        Add   DCM300
        Drain20
    End_Repeat
END
MITSONOBU
    BEGIN
    Prime         <SEQ>
    Prime         <ACT1>
    Prime         <ACT2>
    Repeat    4
    Prime         <SEQ>
    Prime         <ACT1>
    Prime         <ACT2>
        Add   <ACT1>75+<SEQ>75+<ACT2>75
        Wait 3600
        Drain20
    End_Repeat
    Repeat      6
        Add   DCM300
        Drain20
    End_Repeat
        Repeat7
        Add   DMF300
        Drain20
    Repeat      8
        Add DCM   300
        Drain20
    End_Repeat
END
REMOVE_XNBS
    BEGIN
    Next_Sequence
    Prime         mercaptoacetic acid
    Repeat      4
    Prime         mercaptoacetic acid
        Add   mercaptoacetic acid200
        Wait 600
        Drain20
    End_Repeat
    Repeat      4
        Add   DMF200
        Drain20
    End_Repeat
    Repeat      4
        Add   DIOXANE200
        Drain20
    End_Repeat
    Repeat      4
        Add   DMF200
        Drain20
    End_Repeat
    Repeat      5
        Add   DCM200
        Drain20
    End_Repeat
    Repeat      4
        Add   DMF200
        Drain20
    End_Repeat
END
FUNCTIONALIZE_R4
BEGIN
    Next_Sequence
    Prime         <SEQ>
    Prime         <ACT1>
    Repeat      4
        Add   <SEQ>110+<ACT1>100
        Wait 2700
        Drain20
    End_Repeat
    Repeat      6
        Add   DMF300
        Drain20
    End_Repeat
END
TEOC_REMOVAL
BEGIN
    Repeat      4
        Add   TBAF200
        Wait 900
        Drain20
    End_Repeat
    Repeat      5
        Add   DMF200
        Drain20
    End_Repeat
    Repeat      5
        Add   DCM200
        Drain20
    End_Repeat
    Repeat      5
        Add   DMF200
        Drain20
    End_Repeat
```

-continued

```
END
FUNCTIONALIZE_R5
BEGIN
    Next_Sequence
    Prime        <SEQ>
    Prime        <ACT1>
    Repeat    4
        Add    <SEQ>110+<ACT1>100
        Wait 1200
        Drain20
    End_Repeat
END
END_WASH
BEGIN
    Repeat    8
        Add   DMF300
        Drain20
    End_Repeat
    Repeat    8
        Add   DCM300
        Drain20
    End_Repeat
END
```

An additional controller sequence and reagent table files are constructed from any series of reagents as specified in the Brennan et al (supra) such that the synthesizer automatically assembles the desired compounds using the above command file. This is accomplished by choosing a set of reagents to use, loading them into the appropriate bottles in the appropriate concentration, specifying this information into the reagent table file, and finally specifying the order of addition of reagents to each synthesis vessel in the sequence file. Appropriate reagents include: carboxylic acids, acid halides, sulfonyl halides, and isocyanates for $R_3$; and aldehydes, ketones, alkyl halides, aryl halides, carboxylic acids, acid halides, sulfonyl halides, isocyanates, and activated guanylating agents such as bis(BOC)guanyl pyrazole for $R_4$ and $R_5$.

The following reagent table and sequence files were used to prepare compound 11'c

```
Reagent Table File:
{ GroupName BottleID ID ReagentName FlowRate Concentration}
{_____  _____ __ _____ _____ _____}
         }SOLVENTS
    BEGIN
         65    DIOXANE    DIOXANE    206    1
         67    DCM        DCM        265    1
         66    DMF        DMF        230    1
    END
DEBLOCK
    BEGIN
         26    TBAF       TBAF       120    .2
         25    XNBS       XNBS       150    .2
    END
SULFONYLCHLORIDES
    BEGIN
         28    TSCL       p-toluenesulfonyl chloride
                          270    .2    0.2M DIEA/2:INMP/DCM
    END
CARBOXYLATES
    BEGIN
         21    PACE       phenylacetic acid
                          240    .2    DMF
         20    MTA        m-toluic acid   240
                          .2    DMF
    END
ALCOHOLS
    BEGIN
         18    TCOH       3,3-dimethyl-3-silabutyl
                          4-(hydroxymethyl) piperidinecarboxylate
                          240    1    DCM
    END
ACTIVATORS
    BEGIN
         22    HATU       HATU       225    .2    Activates
                          CARBOXYLATES
         19    TPP        TPP        270    .5    Activates
                          ALCOHOLS
         17    DIAD       DIAD       270    .5    Activates
                          ALCOHOLS
    END
Sequence File:
{    Well   ID    Scale     Sequence            }
{    ____   __    _____     _____            }
1    AL     100   TSCL      TCOH   XNBS   MTA   PACE
```

EXAMPLE 5

Preperation of Resins 12a–12c

Coupling Teoc Protected Scaffold Alcohols 5a–5c to Resin 3

Prior to the reaction, resin 3', triphenylphosphine and the glassware were dried under high vacuum, over $P_2O_5$. Resin 3' (0.37 mmol/g theoretical resin substitution, 6.29 mmol) was then swelled in dichloromethane (100 mL) under Ar in a three neck round bottom flask equipped with a dropping funnel and an overhead stirrer. A solution of triphenylphosphine (10 g, 38 mmol, 6 equiv) in DCM (16 mL) was added to the resin via the dropping funnel with stirring and then a solution of one of heterocyclic alcohols 5a–5c (38 mmol) in dichloromethane (16 mL) also via the dropping funnel. The reaction flask was then cooled in an ice-bath and a solution of diisopropylazo dicarboxylate (DIAD) (7.5 mL, 38 mmol, 6 equiv) in DCM (16 mL) was added dropwise to the reaction flask. After the addition, the stirring was stopped and the ice-bath removed. The reaction was allowed to come to room temperature and left to sit overnight. The next day resin 12' was filtered, washed with DCM, DMF and MeOH and then dried under high vacuum.

To assess the purity of the resin, a portion (100 mg) was treated with a solution of p-toluenesulfonyl chloride/0.2M DIEA in DCM (3 mL). The reaction was left for 4 hours. The resin was then filtered, washed with DCM, DMF and MeOH, dried under high vacuum and then cleaved with 95% TFA/5% $H_2O$ for 1.5 h to give compounds 11'a–11'c, which were characterized by mass spectrometry HPLC analysis. Analytical results are illustrated in table 1 below.

TABLE 1

| resin | yield* (%) | compound | MS-CI, m/z | RP-HPLC ret time / (yield) |
|---|---|---|---|---|
| 12'a | 96 | 11'a | 497 (M+H) | 13.56 / (97%) |
| 12'b | 95 | 11'b | 497 (M+H) | 13.81 / (98%) |
| 12'c | 95 | 11'c | 469 (M+H) | 13.67 / (91%) |

*based on theoretical resin substitution

EXAMPLE 6

Automated Library Preparation—method 2

Resins 12a–12c (incorporating heterocycles 5a–5c respectively) were prepared as described previously, then distributed into a 96 well reaction vessel and loaded onto a parallel array synthesizer as described in Brennan et al (Biotechnol. Bioeng. 1998, 61/1:33–45). The synthesizer was then loaded with the following command file input (saved as a tab-delimited text file):

```
INITIAL_WASH
BEGIN
    Repeat          3
        Add         DCM             300
        Drain       20
    End_Repeat
END
FUNCTIONALIZE_R3
BEGIN
    Next_Sequence
    Prime           <SEQ>
    Prime           <ACT1>
    Repeat          6
        Wait        30
        Prime       <SEQ>
        Prime       <ACT1>
        Add         <SEQ>100 +          <ACT1>100
        Wait        1800
        Drain       20
    End_Repeat
    Repeat          5
        Add         DCM             300
        Drain       20
    End_Repeat
    Repeat          5
        Add         DMF             200
        Drain       20
    End_Repeat
    Repeat          8
        Add         DCM             300
        Drain       20
    End_Repeat
END
REMOVE_XNBS
BEGIN
    Prime           mercaptoacetic acid
    Repeat          10
        Prime       mercaptoacetic acid
        Add         mercaptoacetic acid200
        Wait        600
        Drain       20
    End_Repeat
    Repeat          4
        Add         DMF             200
        Drain       20
    End_Repeat
    Repeat          4
        Add         DIOXANE         200
        Drain       30
    End_Repeat
    Repeat          4
        Add         DMF             200
        Drain       20
    End_Repeat
    Repeat          5
        Add         DCM             200
        Drain       20
    End_Repeat
    Repeat          4
        Add         DMF             200
        Drain       20
    End_Repeat
END
FUNCTIONALIZE_R4
BEGIN
    Next_Sequence
    Prime           <SEQ>
    Prime           <ACT1>
    Repeat          4
        Wait        30
        Add         <SEQ>   110 +       <ACT1>100
        Wait        2700
        Drain       20
    End_Repeat
    Repeat          6
        Add         DMF             300
        Drain       20
    End_Repeat
END
```

```
TEOC REMOVAL
BEGIN
    Prime   TBAF
    Repeat  4
        Prime       TBAF
        Add         TBAF            200
        Wait        900
        Drain       20
    End_Repeat
    Repeat          5
        Add         DMF             200
        Drain       20
    End_Repeat
    Repeat          5
        Add         DCM             200
        Drain       20
    End_Repeat
    Repeat          5
        Add         DMF             200
        Drain       20
    End_Repeat
END
FUNCTIONALIZE_R5
BEGIN
    Next_Sequence
    Prime           <SEQ>
    Prime           <ACT1>
    Repeat          4
        Wait        30
        Add         <SEQ>   110 +       <ACT1>100
        Wait        1200
        Drain       20
    End_Repeat
END
END_WASH
BEGIN
    Repeat          8
        Add         DMF             300
        Drain       20
    End_Repeat
    Repeat          8
        Add         DCM             300
        Drain       20
    End_Repeat
END
```

The additional controller sequence and reagent table files are constructed from any series of reagents as specified in the Brennan reference such that the synthesizer automatically assembles the desired compounds using the above command file. This is accomplished by choosing a set of reagents to use, loading them into the appropriate bottles in the appropriate concentration, specifying this information into the reagent table file, and finally specifying the order of addition of reagents to each synthesis vessel in the sequence file. Appropriate reagents include: carboxylic acids, acid halides, sulfonyl halides, and isocyanates for $R_3$; and aldehydes, ketones, alkyl halides, aryl halides, carboxylic acids, acid halides, sulfonyl halides, isocyanates, and activated guanylating agents such as bis(BOC)guanyl pyrazole for $R_4$ and $R_5$.

The following was a reagent table for automated synthesis:

```
{EDA scaffold}
{       Mixture     }
{       2,2-dimethyl-5-oxo-1,3-dioxolane-4-acetyl
        0.5 M               DIEA/DMF        0.220   }
{       BEGIN       }
{               (R)-(-)-2,2-dimethyl-5-oxo-1,3-dioxolane-4-
acetic acid     0.110           174.151             }
```

-continued

```
{           (S)-(+)-2,2-dimethyl-5-oxo-1,3-dioxolane-4-
acetic          acid       0.110    174.151        }
{       END    }
{       EDA support mix           5.000           }
{       BEGIN     }
{           (R)-3-MePipEDA-AG-MB        1.000  621.8072
}
{           (R)-3-PyrEDA-AG-MB          1.000  593.7534
}
{           (S)-3-MePipEDA-AG-MB        1.000  621.8072
}
{           (S)-3-PyrEDA-AG-MB          1.000  593.7534
}
{           4-MePipEDA-AG-MB            1.000  621. 8072
}
{       END    }
{    End Mixtures       }
Empty
        BEGIN
            0      EMPTY     EMPTY    500   1.00
        END
Nalidixic Acid
        BEGIN
            0    nalidixic acid   nalidixic acid
200     0.22            0.22 M
        HATU/0.5 M collidine/DMF           232.238
        END
R-X
        BEGIN
            0    2-bromoacetamide    2-bromoacetamide
200                     1.00      DMF + 2 M DIEA
137.964
            0   Di-tert-butyl dicarbonate      Di-tert-butyl
                                    dicarbonate
200    0.22         0.5 M DIEA/DMF       218.247
        END
RC=O
        BEGIN
            0    isobutyraldehyde      isobutyraldehyde
200                     1.00         3:1
MeOH/TMOF+5% AcOH         72.10619
            0    3-pyridinecarboxaldehyde       3-
pyridinecarboxaldehyde     200   1.00      3:1
                                       MeOH/TMOF+5% AcOH
107.112
            0   N-ethyl-3-carbazolecarboxaldehyde
N-ethyl-3-
carbazolecarboxaldehyde    200  1.00       3:1
                                       MeOH/TMOF+5% AcOH
223.274
        END
RCO2H
        BEGIN
            0    2,2-dimethyl-5-oxo-1,3-dioxolane-4-acetyl
                 2,2-dimethyl-5-oxo-1,3-
dioxolane-4-acetyl                   200
0.22 0.5 M DIEA/DMF
            0   N-BOC-L-homoserine   N-BOC-L-homoserine
200                      0.22    0.5 M DIEA/DMF
219.235
            0   BOC-isonipecotic acid       BOC-
isonipecotic acid          200      0.22
0.5 M DIEA/DMF     229.274
            0   bis (BOC-3, 5-diaminobenzoic acid)
bis (BOC-3,5-                           diaminobenzoic
acid)     200    0.22           0.5 M
                  DIEA/DMF  352.3881
            0    benzofurazan-5-carboxylic acid
                                       benzofurazan-
5-carboxylic acid     200      0.22
                 0.5 M DIEA/DMF     164.12
            0   hydantoic acid      hydantoic acid
200     0.22            0.5 M
            DIEA/DMF   118.091
            0   BOC-imidazole-4-carboxylic acid
BOC-                                  imidazole-4-
carboxylic acid     200     0.22  0.5 M
                  DIEA/DMF     212.2056
            0   5-hydantoinacetic acid             5-
hydantoinacetic acid                       200
0.22 0.5 M DIEA/DMF       158.112
            0    orotic acid      orotic acid
200   0.22           0.5 M
                 DIEA/DMF   156.097
            0    niflumic acid    niflumic acid
200   0.22           0.5 M
                 DIEA/DMF   282.22
            0    2,6-dichloroisonicotinic acid
2,6-
dichloroisonicotinic acid          200       0.22
0.5 M                        DIEA/DMF
192.001
            0    thymine-1-acetic acid     thymine-1-
acetic acid          200  0.22       0.5 M DIEA/DMF
184.15
        END
RCO2H AE
        BEGIN
            0    BOC-isonipecotic acid-2         BOC-
isonipecotic acid                   200       0.22
0.22 M HATU/0.22 M collidine/DMF
229.274
            0    bis(BOC-3,5-diaminobenzoic acid)~2
bis (BOC-3,5-                           diaminobenzoic
acid)     200    0.22          0.22 M
               HATU/0.22 M collidine/DMF  352.3881
            0    BOC-imidazole-4-carboxylic acid~2
BOC-                                  imidazole-4-
carboxylic acid         200        0.22   0.22 M
           HATU/0.22 M collidine/DMF  212.2056
            0    t-butoxyacetic acid  t-butoxyacetic acid
200                      0.22        0.22 M
HATU/0.22 M collidine/DMF
132.1598
            0    anthraquinone-2-carboxylic acid
                                           anthraquinone-
2-carboxylic acid      200       0.22
0.22 M HATU/0.22 M collidine/DMF
252.224
            0   3-(trifluoromethyl)benzoic acid
3-
(trifluoromethyl)benzoic acid        200 0.22         0.22 M
                 HATU/0.22 M collidine/DMF
190. 12
            0    isovaleric acid       isovaleric acid
200                      0.22        0.22 M
HATU/0.22 M collidine/DMF    102.132
            0    2-pyrazinecarboxylic acid       2-
pyrazinecarboxylic acid         200       0.22       0.22 M
                              HATU/0.22 M collidine/DMF
124.099
            0    nalidixic acid~2    nalidixic acid
200 0.22
0.22 M HATU/0.22 M collidine/DMF      232.238
            0    BOC-beta-ALA-OH     BOC-beta-ALA-OH
200                      0.22        0.22 M
HATU/0.22 M collidine/DMF    189.21
            0    thymine-1-acetic acid~2     thymine-1-
acetic acid                  200       0.22       0.22 M
HATU/0.22 M collidine/DMF
184.15
        END
RNCO
        BEGIN
            0    3,5-bis(trifluoromethyl)phenyl isocyanate
                                            3,5-
bis(trifluoromethyl)phenyl isocyanate
200           0.20            DMF 255.117
            0    4-methoxybenzyl isocyanate
4-methoxybenzyl                       isocyanate
200   0.20           DMF   163.175
        END
Support
        BEGIN
            0    EDA support mix     EDA support mix
1                                     5.00
        END
guanyl
```

-continued

```
         BEGIN
             0   1H-pyrazole-1-carboxamidine-HCl
         1H-pyrazole-                           1-
carboxamidine-HCl  50          2.00            DMF + 2 M DIEA
                                               146.58
         END
Activators
         BEGIN
             0   HATU          HATU            200    0.22   DMF
         380.2333              Activates
                               RCO2H
             0   DMAP/DIEA/DMF DMAP/DIEA/DMF
         200    0.20           0.22M
                 DIEA/DMF      122.1699         Activates
                               RCO2H AE
             0   borane-pyridine complex        borane-
pyridine                             complex           200
         1.00  3:1 MeOH/TMOF 92.9362
                               Activates       RC=O
         END
Deprotection
         BEGIN
             0   mercaptoacetic acid mercaptoacetic acid
         150                                   0.50  DMF+1M DBU
         92.11868
             0   TBAF          TBAF            100  0.20    NMP
         261. 468
         END
Solvents
         BEGIN
             0   DCM           DCM             280   1.00
         84.93294
             0   DMF           DMF             200   1.00
         73.09489
             0   dioxane       dioxane         200          1.00
             88. 10632
         END
```

The following sequence file was used in combination with the above reagent table file to prepare a plate of 96 compounds:

1  17921  10.0  4-MePipEDA-AG-MB 2-pyrazinecarboxylic acid cyclopropanecarboxylic acid thymine-1-acetic acid
2  17922  10.0  4-MePipEDA-AG-MB p-tolyl isocyanate cyclopropanecarboxylic acid phenylacetic acid
3  17923  10.0  4-MePipEDA-AG-MB 4-methoxybenzyl isocyanate cyclopropanecarboxylic acid m-toluic acid
4  17924  10.0  4-MePipEDA-AG-MB p-toluenesulfonyl chloride cyclopropanecarboxylic acid t-butoxyacetic acid
5  17953  10.0  (R,S)-3MePipEDA 2-pyrazinecarboxylic acid cyclopropanecarboxylic acid thymine-1-acetic acid
6  17954  10.0  (R,S)-3MePipEDA p-tolyl isocyanate cyclopropanecarboxylic acid phenylacetic acid
7  17955  10.0  (R,S)-3MePipEDA 4-methoxybenzyl isocyanate cyclopropanecarboxylic acid m-toluic acid
8  17956  10.0  (R,S)-3MePipEDA p-toluenesulfonyl chloride cyclopropanecarboxylic acid t-butoxyacetic acid
9  17985  10.0  (RS)-3-PyrEDA 2-pyrazinecarboxylic acid cyclopropanecarboxylic acid thymine-1-acetic acid
10  17986  10.0  (RS)-3-PyrEDA p-tolyl isocyanate cyclopropanecarboxylic acid phenylacetic acid
11  17987  10.0  (RS)-3-PyrEDA 4-methoxybenzyl isocyanate cyclopropanecarboxylic acid m-toluic acid
12  17988  10.0  (RS)-3-PyrEDA p-toluenesulfonyl chloride cyclopropanecarboxylic acid t-butoxyacetic acid
13  17925  10.0  4-MePipEDA-AG-MB 2-pyrazinecarboxylic acid 4-tert-butylbenzoic acid phenylacetic acid
14  17926  10.0  4-MePipEDA-AG-MB p-tolyl isocyanate 4-tert-butylbenzoic acid m-toluic acid
15  17927  10.0  4-MePipEDA-AG-MB 4-methoxybenzyl isocyanate 4-tert-butylbenzoic acid t-butoxyacetic acid
16  17928  10.0  4-MePipEDA-AG-MB p-toluenesulfonyl chloride 4-tert-butylbenzoic acid thymine-1-acetic acid
17  17957  10.0  (R,S)-3MePipEDA 2-pyrazinecarboxylic acid 4-tert-butylbenzoic acid phenylacetic acid
18  17958  10.0  (R,S)-3MePipEDA p-tolyl isocyanate 4-tert-butylbenzoic acid m-toluic acid
19  17959  10.0  (R,S)-3MePipEDA 4-methoxybenzyl isocyanate 4-tert-butylbenzoic acid t-butoxyacetic acid
20  17960  10.0  (R,S)-3MePipEDA p-toluenesulfonyl chloride 4-tert-butylbenzoic acid thymine-1-acetic acid
21  17989  10.0  (RS)-3-PyrEDA 2-pyrazinecarboxylic acid 4-tert-butylbenzoic acid phenylacetic acid
22  17990  10.0  (RS)-3-PyrEDA p-tolyl isocyanate 4-tert-butylbenzoic acid m-toluic acid
23  17991  10.0  (RS)-3-PyrEDA 4-methoxybenzyl isocyanate 4-tert-butylbenzoic acid t-butoxyacetic acid
24  17992  10.0  (RS)-3-PyrEDA p-toluenesulfonyl chloride 4-tert-butylbenzoic acid thymine-1-acetic acid
25  17929  10.0  4-MePipEDA-AG-MB 2-pyrazinecarboxylic acid phenylacetic acid~2 m-toluic acid
26  17930  10.0  4-MePipEDA-AG-MB p-tolyl isocyanate phenylacetic acid~2 t-butoxyacetic acid
27  17931  10.0  4-MePipEDA-AG-MB 4-methoxybenzyl isocyanate phenylacetic acid~2 thymine-1-acetic acid
28  17932  10.0  4-MePipEDA-AG-MB p-toluenesulfonyl chloride phenylacetic acid~2 phenylacetic acid
29  17961  10.0  (R,S)-3MePipEDA 2-pyrazinecarboxylic acid phenylacetic acid~2 m-toluic acid
30  17962  10.0  (R,S)-3MePipEDA p-tolyl isocyanate phenylacetic acid~2 t-butoxyacetic acid
31  17963  10.0  (R,S)-3MePipEDA 4-methoxybenzyl isocyanate phenylacetic acid~2 thymine-1-acetic acid
32  17964  10.0  (R,S)-3MePipEDA p-toluenesulfonyl chloride phenylacetic acid~2 phenylacetic acid
33  17993  10.0  (RS)-3-PyrEDA 2-pyrazinecarboxylic acid phenylacetic acid~2 m-toluic acid
34  17994  10.0  (RS)-3-PyrEDA p-tolyl isocyanate phenylacetic acid~2 t-butoxyacetic acid
35  17995  10.0  (RS)-3-PyrEDA 4-methoxybenzyl isocyanate phenylacetic acid~2 thymine-1-acetic acid
36  17996  10.0  (RS)-3-PyrEDA p-toluenesulfonyl chloride phenylacetic acid~2 phenylacetic acid
37  17933  10.0  4-MePipEDA-AG-MB 2-pyrazinecarboxylic acid m-toluic acid~2 t-butoxyacetic acid
38  17934  10.0  4-MePipEDA-AG-MB p-tolyl isocyanate m-toluic acid~2 thymine-1-acetic acid
39  17935  10.0  4-MePipEDA-AG-MB 4-methoxybenzyl isocyanate m-toluic acid~2 phenylacetic acid
40  17936  10.0  4-MePipEDA-AG-MB p-toluenesulfonyl chloride m-toluic acid~2 m-toluic acid
41  17965  10.0  (R,S)-3MePipEDA 2-pyrazinecarboxylic acid m-toluic acid~2 t-butoxyacetic acid
42  17966  10.0  (R,S)-3MePipEDA p-tolyl isocyanate m-toluic acid~2 thymine-1-acetic acid
43  17967  10.0  (R,S)-3MePipEDA 4-methoxybenzyl isocyanate m-toluic acid~2 phenylacetic acid 44 17968 10.0 (R,S)-3MePipEDA p-toluenesulfonyl chloride m-toluic acid~2 m-toluic acid
45 17997 10.0 (RS)-3-PyrEDA 2-pyrazinecarboxylic acid m-toluic acid~2 t-butoxyacetic acid
46 17998 10.0 (RS)-3-PyrEDA p-tolyl isocyanate m-toluic acid~2 thymine-1-acetic acid
47 17999 10.0 (RS)-3-PyrEDA 4-methoxybenzyl isocyanate m-toluic acid~2 phenylacetic acid
48 18000 10.0 (RS)-3-PyrEDA p-toluenesulfonyl chloride m-toluic acid~2 m-toluic acid
49 17937 10.0 4-MePipEDA-AG-MB 2-pyrazinecarboxylic acid 4-methoxybenzyl isocyanate thymine-1-acetic acid
50 17938 10.0 4-MePipEDA-AG-MB p-tolyl isocyanate 4-methoxybenzyl isocyanate phenylacetic acid
51 17939 10.0 4-MePipEDA-AG-MB 4-methoxybenzyl isocyanate 4-methoxybenzyl isocyanate m-toluic acid
52 17940 10.0 4-MePipEDA-AG-MB p-toluenesulfonyl chloride 4-methoxybenzyl isocyanate t-butoxyacetic acid
53 17969 10.0 (R,S)-3MePipEDA 2-pyrazinecarboxylic acid 4-methoxybenzyl isocyanate thymine-1-acetic acid
54 17970 10.0 (R,S)-3MePipEDA p-tolyl isocyanate 4-methoxybenzyl isocyanate phenylacetic acid
55 17971 10.0 (R,S)-3MePipEDA 4-methoxybenzyl isocyanate 4-methoxybenzyl isocyanate m-toluic acid
56 17972 10.0 (R,S)-3MePipEDA p-toluenesulfonyl chloride 4-methoxybenzyl isocyanate t-butoxyacetic acid
57 18001 10.0 (RS)-3-PyrEDA 2-pyrazinecarboxylic acid 4-methoxybenzyl isocyanate thymine-1-acetic acid
58 18002 10.0 (RS)-3-PyrEDA p-tolyl isocyanate 4-methoxybenzyl isocyanate phenylacetic acid
59 18003 10.0 (RS)-3-PyrEDA 4-methoxybenzyl isocyanate 4-methoxybenzyl isocyanate m-toluic acid
60 18004 10.0 (RS)-3-PyrEDA p-toluenesulfonyl chloride 4-methoxybenzyl isocyanate t-butoxyacetic acid
61 17941 10.0 4-MePipEDA-AG-MB 2-pyrazinecarboxylic acid t-butoxyacetic acid~2 phenylacetic acid
62 17942 10.0 4-MePipEDA-AG-MB p-tolyl isocyanate t-butoxyacetic acid~2 m-toluic acid
63 17943 10.0 4-MePipEDA-AG-MB 4-methoxybenzyl isocyanate t-butoxyacetic acid~2 t-butoxyacetic acid
64 17944 10.0 4-MePipEDA-AG-MB p-toluenesulfonyl chloride t-butoxyacetic acid~2 thymine-1-acetic acid
65 17973 10.0 (R,S)-3MePipEDA 2-pyrazinecarboxylic acid t-butoxyacetic acid~2 phenylacetic acid
66 17974 10.0 (R,S)-3MePipEDA p-tolyl isocyanate t-butoxyacetic acid~2 m-toluic acid
67 17975 10.0 (R,S)-3MePipEDA 4-methoxybenzyl isocyanate t-butoxyacetic acid~2 t-butoxyacetic acid
68 17976 10.0 (R,S)-3MePipEDA p-toluenesulfonyl chloride t-butoxyacetic acid~2 thymine-1-acetic acid
69 18005 10.0 (RS)-3-PyrEDA 2-pyrazinecarboxylic acid t-butoxyacetic acid~2 phenylacetic acid
70 18006 10.0 (RS)-3-PyrEDA p-tolyl isocyanate t-butoxyacetic acid~2 m-toluic acid
71 18007 10.0 (RS)-3-PyrEDA 4-methoxybenzyl isocyanate t-butoxyacetic acid~2 t-butoxyacetic acid
72 18008 10.0 (RS)-3-PyrEDA p-toluenesulfonyl chloride t-butoxyacetic acid~2 thymine-1-acetic acid
73 17945 10.0 4-MePipEDA-AG-MB 2-pyrazinecarboxylic acid BOC-4-ABZOH m-toluic acid
74 17946 10.0 4-MePipEDA-AG-MB p-tolyl isocyanate BOC-4-ABZOH t-butoxyacetic acid
75 17947 10.0 4-MePipEDA-AG-MB 4-methoxybenzyl isocyanate BOC-4-ABZOH thymine-1-acetic acid
76 17948 10.0 4-MePipEDA-AG-MB p-toluenesulfonyl chloride BOC-4-ABZOH phenylacetic acid
77 17977 10.0 (R,S)-3MePipEDA 2-pyrazinecarboxylic acid BOC-4-ABZOH m-toluic acid
78 17978 10.0 (R,S)-3MePipEDA p-tolyl isocyanate BOC-4-ABZOH t-butoxyacetic acid
79 17979 10.0 (R,S)-3MePipEDA 4-methoxybenzyl isocyanate BOC-4-ABZOH thymine-1-acetic acid
80 17980 10.0 (R,S)-3MePipEDA p-toluenesulfonyl chloride BOC-4-ABZOH phenylacetic acid
81 18009 10.0 (RS)-3-PyrEDA 2-pyrazinecarboxylic acid BOC-4-ABZOH m-toluic acid
82 18010 10.0 (RS)-3-PyrEDA p-tolyl isocyanate BOC-4-ABZOH t-butoxyacetic acid
83 18011 10.0 (RS)-3-PyrEDA 4-methoxybenzyl isocyanate BOC-4-ABZOH thymine-1-acetic acid
84 18012 10.0 (RS)-3-PyrEDA p-toluenesulfonyl chloride BOC-4-ABZOH phenylacetic acid
85 17949 10.0 4-MePipEDA-AG-MB 2-pyrazinecarboxylic acid p-tolyl isocyanate t-butoxyacetic acid
86 17950 10.0 4-MePipEDA-AG-MB p-tolyl isocyanate p-tolyl isocyanate thymine-1-acetic acid
87 17951 10.0 4-MePipEDA-AG-MB 4-methoxybenzyl isocyanate p-tolyl isocyanate phenylacetic acid
88 17952 10.0 4-MePipEDA-AG-MB p-toluenesulfonyl chloride p-tolyl isocyanate m-toluic acid
89 17981 10.0 (R,S)-3MePipEDA 2-pyrazinecarboxylic acid p-tolyl isocyanate t-butoxyacetic acid
90 17982 10.0 (R,S)-3MePipEDA p-tolyl isocyanate p-tolyl isocyanate thymine-1-acetic acid
91 17983 10.0 (R,S)-3MePipEDA 4-methoxybenzyl isocyanate p-tolyl isocyanate phenylacetic acid
92 17984 10.0 (R,S)-3MePipEDA p-toluenesulfonyl chloride p-tolyl isocyanate m-toluic acid
93 18013 10.0 (RS)-3-PyrEDA 2-pyrazinecarboxylic acid p-tolyl isocyanate t-butoxyacetic acid
94 18014 10.0 (RS)-3-PyrEDA p-tolyl isocyanate p-tolyl isocyanate thymine-1-acetic acid
95 18015 10.0 (RS)-3-PyrEDA 4-methoxybenzyl isocyanate p-tolyl isocyanate phenylacetic acid
96 18016 10.0 (RS)-3-PyrEDA p-toluenesulfonyl chloride p-tolyl isocyanate m-toluic acid

EXAMPLE 7

Biological Assays

1) *Staphylococcus aureus* Antimicrobial Assay

*Staphylococcus aureus* is known to cause localized skin infections as a result of poor hygiene, minor trauma, psoriasis or eczema. It also causes respiratory infections, pneumonia, toxic shock syndrome and septicemia. It is a common cause of acute food poisoning. It exhibits rapid emergence of drug resistance to penicillin, cephalosporin, vancomycin and nafcillin.

In this assay, the strain *S. aureus* ATCC 25923 (American Type Culture Collection) is used. To initiate the exponential phase of bacterial growth prior to the assay, a sample of bacteria grown overnight at 37° C. in typtocase soy broth (BBL). This bacteria is then used to reinoculate sample wells of 96-well microtiter plates. The assays are carried out in the 96-well microtiter plates in 150 μL volume with approximately 1×10$^{-6}$ cells per well.

Bacteria in typtocase soy broth (75 μL) is added to the compound mixtures in solution in 75 μL water/4% DMSO in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

2) *Streptococcus Pyogenes* Antimicrobial Assay

In this assay, the strain *S. pyogenes* ATCC 14289 (American Type Culture Collection) is used. To initiate the exponential phase of bacterial growth prior to the assay, a sample of bacteria is grown overnight at 37° C. in 1× Todd-Hewitt broth. This bacteria is then used to reinoculate sample wells of 96-well microtiter plates. The assays are carried out in the 96-well microtiter plates in 150 μL volume with approximately 1×10$^6$ cells per well.

Bacteria in 1× Todd-Hewitt broth (75 μL) is added to the compound mixtures in solution in 75 μL water in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

3) *E. coli* imp-antimicrobial Assay

In this assay, the strain *E. coli* imp-obtained from Spenser Bensen (Sampson, B. A., Misra, R. & Benson, S. A. (1989), *Genetics*, 122, 491–501, Identification and characterization of a new gene of *Escherichia coli* K-12 involved in outer membrane permeability) is used. To initiate the exponential phase of bacterial growth prior to the assay, a sample of bacteria was grown overnight at 37° C. in Luria broth and then used to reinoculate sample wells of 96-well microtiter plates. The assays were carried out in the 96-well microtiter plates in 150 μL volume with approximately 1×10$^6$ cells per well.

Bacteria in Luria broth (75 μL) was added to the compound mixtures in solution in 75 μL water in the individual well of the microtiter plate. Final concentrations of the compound mixtures were 25 μM, 10 μM and 1 μM. Each concentration of the compound mixtures were assayed in triplicate. The plates were incubated at 37° C. and growth monitored over a 24 hour period by measuring the optical density at 595 nm using a BioRad model 3550 UV microplate reader. The percentage of growth relative to a well containing no compound was determined. Ampicillin and tetracycline antibiotic positive controls were concurrently tested in each screening assay. Results of testing some of the compounds of the invention at 500 μM concentration are presented in table 2 below as % inhibition of bacterial growth in culture.

4) *C. albicans* Antifungal Assay

In this assay, the strain *C. albicans* ATCC 10231 (American Type Culture Collection) is used. To initiate the exponential phase of yeast growth prior to the assay, a sample of yeast is grown overnight at 37° C. in YM media. This yeast is then used to reinoculate sample wells of 96-well microtiter plates. The assays are carried out in the 96-well microtiter plates in 150 μL volume with approximately 1×10$^6$ cells per well.

Yeast in YM media (75 μL) is added to the compound mixtures in solution in 75 μL water in the individual well of the microtiter plate. Final concentrations of the compound mixtures are 25 μM, 10 μM and 1 μM. Each concentration of the compound mixtures are assayed in triplicate. The plates are incubated at 37° C. and growth onitored over a 24 hour period by measuring the optical density at 595 nm using a BioRad model 3550 UV microplate reader. The percentage of growth relative to a well containing no compound is determined. Amphotericin B positive control is concurrently tested in each screening assay.

5) tat/TAR Inhibition Assay

The effects of combinatorial libraries, and individual members thereof, on HIV tat/TAR, RNA/protein interactions are examined using a rapid and reproducible binding assay. The assay consists of a biotinylated truncated version of the HIV-1 TAR stem-loop, which is anchored to the wells of a 96 well ELISA plate which has been coated with streptavidin. The TAR RNA is recognized by the HIV-1 protein tat and the amount of tat bound is quantitated using an antibody raised against tat and a secondary antibody conjugated to an alkaline phosphatase or HRP enzyme to produce a colorimetric reaction.

Materials:

A 39 residue tat peptide (aa 49-85 of HIV tat protein). This is the C terminal basic binding domain of the tat protein. This peptide was synthesized by a contract lab.

A 30 base RNA oligonucleotide consisting of the bulge and stem/loop structure of HIV TAR which has also been Biotin conjugated. This RNA oligonucleotide was synthesized in house.

A biotinylated HIV RRE RNA oligonucleotide synthesized in house.

Binding buffer: 40 mM Tris-HCl (pH 8.0), 0.01% NP-40, 20% glycerol, 1.5 mM MgCl, 0.01% NaN3, 50 mM KCl.

Streptavidin coated 96 well microtitre plates (Elkay Labsystems).

Protein A/G alkaline phosphatase (Pierce).

Anti tat antiserum (BioDesign).

PNPP substrate (Pierce).

Methods:

To each well of a Streptavidin coated 96 well ELISA plate is added 200 μl of a solution of the 30 base TAR sequence (20 nM) in binding buffer. The plate is incubated at 4° C. for 1 hour. The biotintylated HIV RRE RNA oligonucleotide is bound to selected wells as a negative control RNA. The plate is washed with binding buffer three times and 100 μl of a 100 nM solution of the 39 residue tat peptide in binding buffer is added to each well.

Combinatorial libraries as mixtures, or discrete members thereof, are added to selected wells of the plate at initial concentrations of 100 μM. The plate is incubated for 1 hour at room temperature.

The plate is washed with binding buffer three times and blocked with binding buffer+5% FCS. 100 μl of tat antiserum diluted 1:700 in binding buffer is added to the wells of the plate and the plate is incubated for 1.5 hours at 4° C. The plate is washed three times with binding buffer and 150 μL of a solution of protein A/G alkaline phosphatase diluted 1:5000 in binding buffer is added to each well. The plate is incubated for 1.5 hours at 4° C. followed by washing three times with binding buffer. 150 μL of PNPP substrate is added to each well and the plate is incubated for 1 hour at 37° C. The absorbance of each well is read in a multiwell plate reader.

6) Bacterial DNA Gyrase Antimicrobial Mechanistic Asay

DNA gyrase is a bacterial enzyme which can introduce negative supercoils into DNA utilizing the energy derived from ATP hydrolysis. This activity is critical during DNA replication and is a well characterized target for antibiotic inhibition of bacterial growth. In this assay, libraries of compounds are screened for inhibition of DNA gyrase. The assay measures the supercoiling of a relaxed plasmid by DNA gyrase as an electrophoretic shift on an agarose gel. Initially all libraries are screened for inhibitory activity at 30 μL and then a dose response analysis is effected with active compounds. Novobiocin, an antibiotic that binds to the β subunit of DNA gyrase is used as a positive control in the assay. The sensitivity of the DNA gyrase assay was determined by titrating the concentration of the know DNA gyrase inhibitor, Novobiocin, in the supercoiling assay. The $IC_{50}$ was determined to be 8 nM, sufficient to identify the activity of a single active species of comparable activity in a library having 30 μM concentration.

7) Metal Chelator/imaging Assay

This procedure is used to identify compounds of the invention from libraries of compounds constructed to include a ring that contains an ultraviolet chromophore. Further the chemical functional groups attached to the compounds of the invention are selected from metal binders, coordinating groups such as amine, hydroxyl and carbonyl groups, and other groups having lone pairs of electrons, such that the compounds of the invention can form coordination complexes with heavy metals and imaging agents. The procedure is used to identify compounds of the invention useful for chelating and removing heavy metals from industrial broths, waste stream eluents, heavy metal poisoning of farm animals and other sources of contaminating heavy metals, and for use in identifying imaging agent carriers, such as carriers for technetium 99.

An aliquot of a test solution having the desired ion or imaging agent at a known concentration is added to an aliquot of standard solution of the library under assay. The UV spectrum of this aliquot is measured and is compared to the UV spectrum of a further aliquot of the same solution lacking the test ion or imaging agent. A shift in the extinction coefficient is indicative of binding of the metal ion or imaging ion to a compound in the library being assayed.

8) $PLA_2$ Inhibition Assay

A target for assay of a combinatorially generated library of compounds is the phospholipase $A_2$ family. Phospholipases $A_2$ ($PLA_2$) are a family of enzymes that hydrolyze the sn-2 ester linkage of membrane phospholipids resulting in release of a free fatty acid and a lysophospholipid (Dennis, E. A., The Enzymes, Vol. 16, pp. 307–353, Boyer, P. D., ed., Academic Press, N.Y., 1983). Elevated levels of type II $PLA_2$ are correlated with a number of human inflammatory diseases. The $PLA_2$-catalyzed reaction is the rate-limiting step in the release of a number of pro-inflammatory mediators. Arachidonic acid, a fatty acid commonly linked at the sn-2 position, serves as a precursor to leukotrienes, prostaglandins, lipoxins and thromboxanes. The lysophospholipid can be a precursor to platelet-activating factor. $PLA_2$ is regulated by pro-inflammatory cytokines and, thus, occupies a central position in the inflammatory cascade (Dennis, ibid.; Glaser et al., *TiPs Reviews* 1992, 14, 92; and Pruzanski et al., *Inflammation* 1992, 16, 451). All mammalian tissues evaluated thus far have exhibited $PLA_2$ activity. At least three different types of $PLA_2$ are found in humans: pancreatic (type I), synovial fluid (type II) and cytosolic. Studies suggest that additional isoenzymes exist. Type I and type II, the secreted forms of $PLA_2$, share strong similarity with phospholipases isolated from the venom of snakes. The $PLA_2$ enzymes are important for normal functions including digestion, cellular membrane remodeling and repair, and in mediation of the inflammatory response. Both cytosolic and type II enzymes are of interest as therapeutic targets. Increased levels of the type II $PLA_2$ are correlated with a variety of inflammatory disorders including rheumatoid arthritis, osteoarthritis, inflammatory bowel disease and septic shock, suggesting that inhibitors of this enzyme would have therapeutic utility. Additional support for a role of $PLA_2$ in promoting the pathophysiology observed in certain chronic inflammatory disorders was the observation that injection of type II $PLA_2$ into the footpad of rats (Vishwanath et al., *Inflammation* 1988, 12, 549) or into the articular space of rabbits (Bomalaski et al., *J. Immunol.* 1991, 146, 3904) produced an inflammatory response. When the protein was denatured before injection, no inflammatory response was produced.

The type II $PLA_2$ enzyme from synovial fluid is a relatively small molecule (about 14 kD) and can be distinguished from type I enzymes (e.g. pancreatic) by the sequence and pattern of its disulfide bonds. Both types of enzymes require calcium for activity. The crystal structures of secreted $PLA_2$ enzymes from venom and pancreatic $PLA_2$, with and without inhibitors, have been reported (Scott et al., *Science* 1990, 250, 1541). Recently, the crystal structure of $PLA_2$ from human synovial fluid has been determined (Wery et al., *Nature* 1991, 352, 79). The structure clarifies the role of calcium and amino acid residues in catalysis. Calcium acts as a Lewis acid to activate the scissile ester carbonyl bond of 1,2-diacylglycerophospholipids and binds to the lipid, and a His-Asp side chain diad acts as a general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft (ca. 14 Å) in the enzyme. The walls of this cleft contact the hydrocarbon portion of the phospholipid and are composed of hydrophobic and aromatic residues. The positively-charged amino-terminal helix is situated above the opening of the hydrophobic cleft. Several lines of evidence suggest that the N-terminal portion is the interfacial binding site (Achari et al., *Cold Spring Harbor Symp. Quant. Biol.* 1987, 52, 441; Cho et al., *J. Biol. Chem.* 1988, 263, 11237; Yang et al., *Biochem. J.* 1989, 262, 855; and Noel et al., *J. Am. Chem. Soc.* 1990, 112, 3704).

Much work has been reported in recent years on the study of the mechanism and properties of $PLA_2$-catalyzed hydrolysis of phospholipids. In in vitro assays, $PLA_2$ displays a lag phase during which the enzyme adsorbs to the substrate bilayer and a process called interfacial activation occurs. This activation may involve desolvation of the enzyme/lipid interface or a change in the physical state of the lipid around the cleft opening. Evidence favoring this hypothesis comes from studies revealing that rapid changes in $PLA_2$ activity occur concurrently with changes in the fluorescence of a membrane probe (Burack et al., *Biochemistry* 1993, 32, 583). This suggests that lipid rearrangement is occurring during the interfacial activation process. $PLA_2$ activity is maximal around the melting temperature of the lipid, where regions of gel and liquid-crystalline lipid coexist. This is also consistent with the sensitivity of $PLA_2$ activity to temperature and to the composition of the substrate, both of which can lead to structurally distinct lipid arrangements separated by a boundary region. Fluorescence microscopy was used to simultaneously identify the physical state of the lipid and the position of the enzyme during catalysis (Grainger et al., *FEBS Lett.* 1989, 252, 73). These studies clearly show that $PLA_2$ binds exclusively at the boundary region between liquid and solid phase lipid. While the hydrolysis of the secondary ester bond of 1,2-diacylglycerophospholipids catalyzed by the enzyme is relatively simple, the mechanistic and kinetic picture is clouded by the complexity of the enzyme-substrate interaction. A remarkable characteristic of $PLA_2$ is that maximal catalytic activity is observed on substrate that is aggregated (i.e. phospholipid above its critical micelle concentration), while low levels of activity are observed on monomeric substrate. As a result, competitive inhibitors of $PLA_2$ either have a high affinity for the active site of the enzyme before it binds to the substrate bilayer or partition into the membrane and compete for the active site with the phospholipid substrate. Although a number of inhibitors appear to show promising inhibition of $PLA_2$ in biochemical assays (Yuan et al., *J. Am. Chem. Soc.* 1987, 109, 8071; Lombardo et al., *J. Biol. Chem.* 1985, 260, 7234; Washburn et al., *J. Biol. Chem.* 1991, 266, 5042; Campbell et al., *J. Chem. Soc., Chem. Commun.* 1988, 1560; and Davidson et al., *Biochem. Biophys. Res. Commun.* 1986, 137, 587), reports describing in vivo activity are limited (Miyake et al., *J. Pharmacol. Exp. Ther.* 1992, 263, 1302).

In one preferred embodiment, compounds of the invention are selected for their potential to interact with, and preferably inhibit, the enzyme $PLA_2$. Thus, compounds of the invention can be used for topical and/or systemic treatment of inflammatory diseases including atopic dermatitis and inflammatory bowel disease. In selecting the functional groups, advantage can be taken of $PLA_2$'s preference for anionic vesicles over zwitterionic vesicles. Preferred compounds of the invention for assay for $PLA_2$ include those having aromatic diversity groups to facilitate binding to the cleft of the $PLA_2$ enzyme (Oinuma et al., *J. Med. Chem.* 1991, 34, 2260; Marki et al., *Agents Actions* 1993, 38, 202; and Tanaka et al., *J. Antibiotics* 1992, 45, 1071). Benzyl and 4-hexylbenzyl groups are preferred aromatic diversity groups. $PLA_2$-directed compounds of the invention can further include hydrophobic functional groups such as tetraethylene glycol groups. Since the $PLA_2$ enzyme has a hydrophobic channel, hydrophobicity is believed to be an important property of inhibitors of the enzyme.

The libraries additionally can be screened in other in vitro assays to determine further mechanisms of inhibition. The libraries are screened for inhibition of $PLA_2$ in the assay using *E. coli* labeled with $^3$H-oleic acid (Franson et al., *J. Lipid Res.* 1974, 15, 380; and Davidson et al., *J. Biol. Chem.* 1987, 262, 1698) as the substrate. Type II $PLA_2$ (originally isolated from synovial fluid), expressed in a baculovirus system and partially purified, serves as a source of the enzyme. A series of dilutions of each of the libraries is performed: 10 μl of each library of compounds is incubated for 5 minutes at room temperature with a mixture of 10 μl $PLA_2$, 20 μl 5× $PLA_2$ Buffer (500 mM Tris 7.0–7.5, 5 mM $CaCl_2$), and 50 μl water. Samples of each library are run in duplicate. At this point, 10 μl of $^3$H *E. coli* cells is added. This mixture is incubated at 37° C. for 15 minutes. The enzymatic reaction is stopped with the addition of 50 μL 2M HCl and 50 μL fatty-acid-free BSA (20 mg/mL PBS), vortexed for 5 seconds, and centrifuged at high speed for 5 minutes. 165 μL of each supernate is then put into a scintillation vial containing 6 ml of scintillant (ScintiVerse) and cpms are measured in a Beckman Liquid Scintillation Counter. As a control, a reaction without the combinatorial pool (or library of compounds) is run alongside the other reactions as well as a baseline reaction containing no compounds of the invention as well as no $PLA_2$ enzyme. CPMs are corrected for by subtracting the baseline from each reaction data point.

Confirmation of the "winners" is made to confirm that a compound of the invention binds to enzyme rather than substrate and that the inhibition by a compound of the invention that is selected is specific for type II $PLA_2$. An assay using $^{14}$C-phosphatidyl ethanolamine ($^{14}$C-PE) as substrate, rather than *E. coli* membrane, is used to insure enzyme rather than substrate specificity. Micelles of $^{14}$C-PE and deoxycholate are incubated with the enzyme and a compound of the invention. $^{14}$C-labeled arachidonic acid released as a result of $PLA_2$-catalyzed hydrolysis is separated from substrate by thin layer chromatography and the radioactive product is quantitated. The "winner" is compared to phosphatidyl ethanolamine, the preferred substrate of human type II $PLA_2$, to confirm its activity. $PLA_2$ from other sources (snake venom, pancreatic, bee venom) and phospholipase C, phospholipase D and lysophospholipase can be used to further confirm that the inhibition is specific for human type II $PLA_2$.

9) Leukotriene $B_4$ Assay

Leukotriene $B_4$ ($LTB_4$) has been implicated in a variety of human inflammatory diseases, and its pharmacological effects are mediated via its interaction with specific surface cell receptors. Library products, either as discrete compounds or as small mixtures of compounds, are screened for competitive inhibition of radiolabeled $LTB_4$ binding to a receptor preparation.

A Nenquest™ Drug Discovery System Kit (NEN Research Products, Boston, Mass.) is used to select an inhibitor of the interaction of Leukotriene $B_4$ ($LTB_4$) with receptors on a preparation of guinea pig spleen membrane. [$^3$H] Leukotriene $B_4$ reagent is prepared by adding 5 mL of ligand diluent (phosphate buffer containing NaCl, $MgCl_2$, EDTA and Bacitracin, pH 7.2) to 0.25 mL of the radioligand. The receptor preparation is made by thawing the concentrate, adding 35 mL of ligand diluent and swirling gently in order to re-suspend the receptor homogeneously. Reagents are kept on ice during the course of the experiment, and the remaining portions are stored at −20 C.

Library products prepared as per the general procedures of examples above are diluted to 5 μM, 50 μM and 500 μM in phosphate buffer (1×PBS, 0.1% azide and 0.1% BSA, pH 7.2), yielding final test concentrations of 0.5 μM, 5 μM and 50 μM, respectively. Samples are assayed in duplicate. [$^3$H] $LTB_4$ (25 μL) is added to 25 μL of either appropriately diluted standard (unlabeled $LTB_4$) or library product. The receptor suspension (0.2 mL) is added to each tube. Samples are incubated at 4 C. for 2 hours. Controls include [$^3$H] $LTB_4$ without receptor suspension (total count vials), and sample of ligand and receptor without library molecules (standard).

After the incubation period, the samples are filtered through GF/B paper that had been previously rinsed with cold saline. The contents of each tube are aspirated onto the filter paper to remove unbound ligand from the membrane preparation, and the tubes washed (2×4 mL) with cold saline. The filter paper is removed from the filtration unit and the filter disks are placed in appropriate vials for scintillation counting. Fluor is added, and the vials shaken and allowed to stand at room temperature for 2 to 3 hours prior to counting. The counts/minute (cpm) obtained for each sample are subtracted from those obtained from the total counts to determine the net cpm for each sample. The degree of inhibition of binding for each library prodcut is determined relative to the standard (sample of ligand and receptor without library product).

TABLE 2

| cmpd | structure | % inhib. |
|---|---|---|
| 17925 | 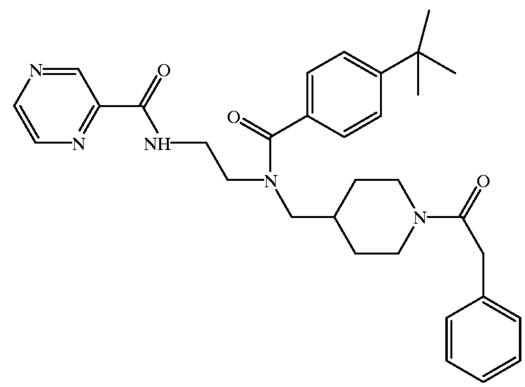 | 93.9 |
| 17927 | 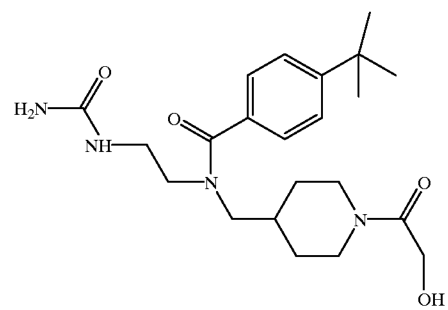 | 96.3 |
| 17928 | 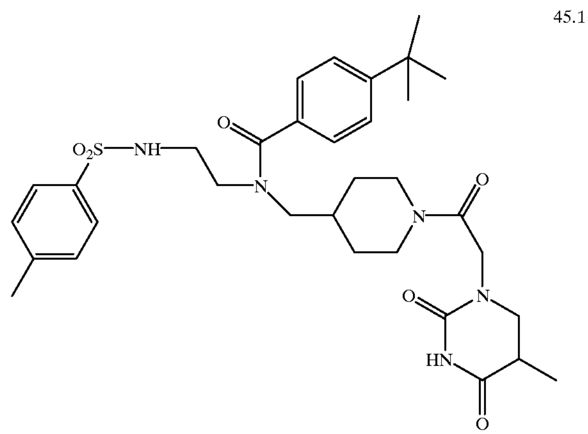 | 45.1 |
| 17946 | 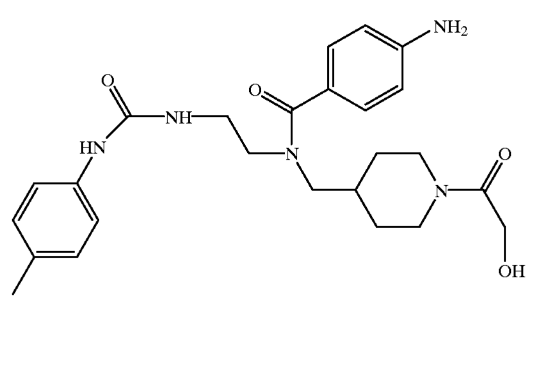 | 98.7 |

TABLE 2-continued
| cmpd | structure | % inhib. |
|---|---|---|
| 17957 | 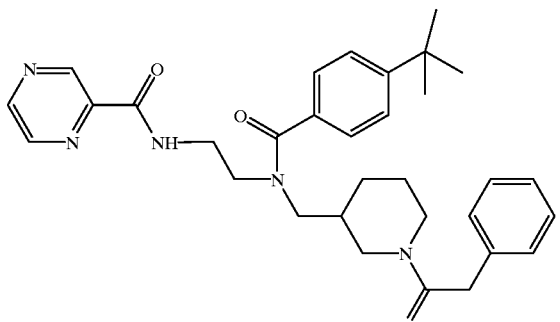 | 95.7 |
| 17959 | 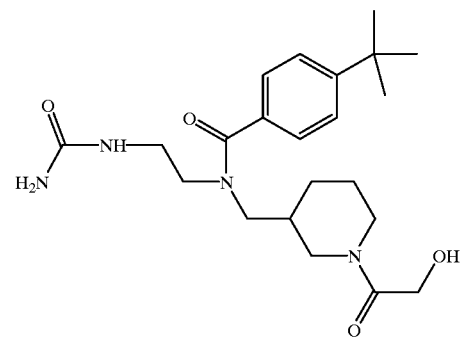 | 39.5 |
| 17982 | 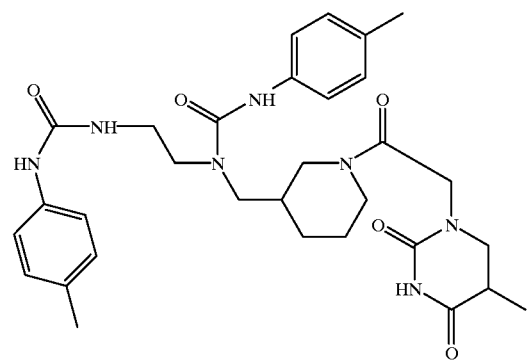 | 84.1 |
| 17985 | 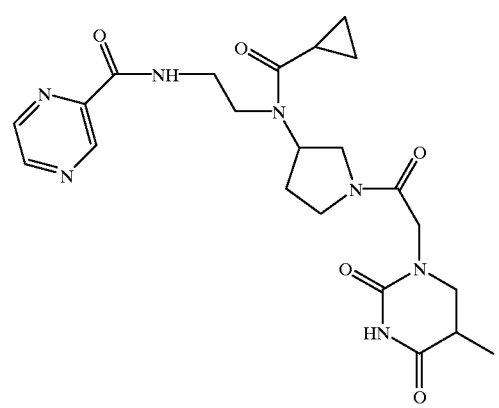 | 43.7 |

TABLE 2-continued
| cmpd | structure | % inhib. |
|---|---|---|
| 17986 | 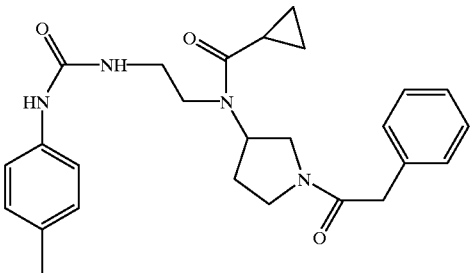 | 35.2 |
| 17989 | 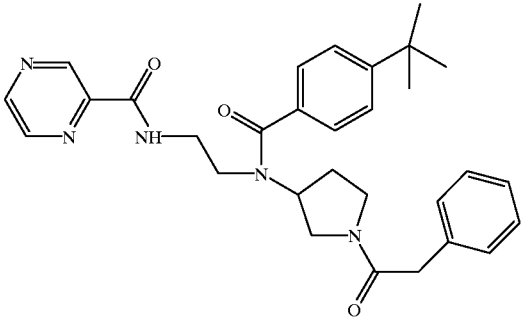 | 38.5 |
| 18005 | 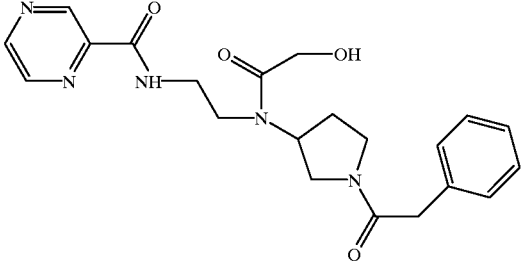 | 61.1 |
| 18010 | 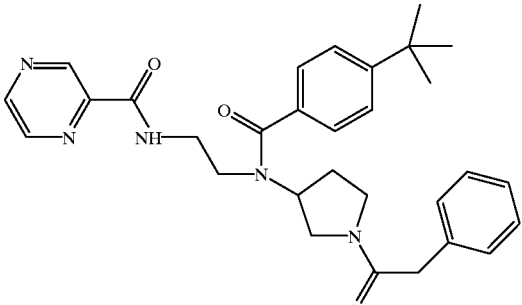 | 99.3 |
*test dose = 500 μM

We claim:
1. A compound of formula:

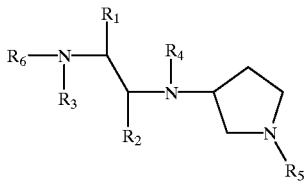

XV wherein:
R₁ and R₂ are independently H or a hydrocarbyl group selected from $C_1$–$C_{10}$ alkyl, $C_2$–$C_{10}$ alkenyl, $C_2$–$C_{20}$ alkynyl, $C_6$–$C_{14}$ aryl, $C_6$–$C_{14}$ aralkyl, $C_3$–$C_{14}$ cycloalkyl, $C_5$–$C_{14}$ fused cycloalkyl, $C_4$–$C_{14}$ heterocyclyl, $C_4$–$C_{14}$ heterocycloalkyl, $C_4$–$C_{14}$ heteroaryl, $C_4$–$C_{14}$ heteroarylalkyl, and CH(R₂)—NH—R₂; wherein said hydrocarbyl group is optionally substituted with acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol or thioalkoxy;

R₃, R₄, and R₅ are independently H, an amino protecting group, or a divalent group selected from CH₂, CH(R₂), C═O, C═S, S(═O)₂, C(═O)NH, C(═S)NH or C(═O)O; wherein said divalent group is substituted with H or a hydrocarbyl group selected from $C_1$–$C_{10}$ alkyl, $C_2$–$C_{10}$ alkenyl, $C_2$–$C_{20}$ alkynyl, $C_6$–$C_{14}$ aryl, $C_6$–$C_{14}$ aralkyl, $C_3$–$C_{14}$ cycloalkyl, $C_5$–$C_{14}$ fused cycloalkyl, $C_4$–$C_{14}$ heterocyclyl, $C_4$–$C_{14}$ heterocyclylalkyl, $C_4$–$C_{14}$ heteroaryl, $C_4$–$C_{14}$ heteroarylalkyl or CH(R₂)—NH—R₂; wherin said hydrocarbyl group is optionally substituted with oxo, acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

R₆ is H or a solid support.

2. A compound according to claim 1, wherein R₁ and R₂ are both H.

3. A compound according to claim 1, wherein R₃ is selected from 2-pyrazine-carboxyl, carboxamidino, 3-(trifluoromethyl)benzoyl, carbamoyl, 2-aminopropionyl, imidizolyl-4-carboxyl, isonipecotyl, 3,5-diaminobenzoyl, isovaleryl, nalidixyl, hydroxyacetyl and thymine-1-acetyl.

4. A compound according to claim 1, wherein R₃ is selected from 2-pyrazine-carboxyl, aminocarbonyl, p-tolylsulfonyl, p-nitrophenyl-carbonyl, and p-tolylaminocarbonyl.

5. A compound according to claim 1, wherein R₄ is selected from H, 2-pyrazine-carboxyl, 3,5-bis (trifluoromethyl)phenylcarbamoyl, 3-(trifluoromethyl) benzoyl, 3-pyridylmethyl, carbamoyl, aminocarbonyl, imidizole-4-carboxyl, isonipecotyl, di-t-butyl-, N-ethyl-3-carbazolylmethyl, anthraquinone-2-carbonyl, 3,5-diaminobenzoyl, isobutyl, isovaleryl, nalidixyl, hydroxyacetyl and thymine-1-acetyl.

6. A compound according to claim 1, wherein R₄ is selected from H, para-t-butyl-phenylcarbonyl, p-aminophenyl-carbonyl, cyclopropyl-carbonyl, 2-hydroxyacetyl and 2-nitrophenyl-sulfonyl.

7. A compound according to claim 1, wherein R₅ is selected from H, (R)-(−)-2,2-dimethyl-5-oxo-1,3-dioxolane-4-acetyl, (S)-(+)-2,2-dimethyl-5-oxo-1,3-dioxolane-4-acetyl, carboxamidino, 2,6-dichloroisonicotinyl, carbamoylmethyl, 3-pyridylmethyl, carbamoyl, 5-hydantoinacetyl, imidazole-4-carboxyl, isonipecotyl, 2-amino-4-hydroxybutyryl, benzo[c]1,2,5-oxadiazole-5-carboxyl, 3,5-diaminobenzoyl, hydantoyl, isobutyl, nalidixoyl, niflumyl, orotyl and thymine-1-acetyl.

8. A compound according to claim 1, wherein R₅ is selected from H, 2-phenylacetyl, 2-hydroxyacetyl, thymine-1-acetyl and 2-trimethylsiylethoxycarbonyl.

* * * * *